United States Patent
Singhal et al.

(10) Patent No.: US 8,086,313 B2
(45) Date of Patent: *Dec. 27, 2011

(54) IMPLANTABLE MEDICAL DEVICE WITH ANTI-INFECTION AGENT

(75) Inventors: Ruchika Singhal, Minneapolis, MN (US); Darren A. Janzig, Centerville, MN (US); Carl D. Wahlstrand, Lino Lakes, MN (US); Robert M. Skime, Coon Rapids, MN (US); Paulette C. Olson, Eagan, MN (US); Erik R. Scott, Maple Grove, MN (US); James E. Randall, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 322 days.

This patent is subject to a terminal disclaimer.

(21) Appl. No.: 12/536,258

(22) Filed: Aug. 5, 2009

(65) Prior Publication Data
US 2009/0292327 A1    Nov. 26, 2009

Related U.S. Application Data

(63) Continuation of application No. 10/837,319, filed on Apr. 30, 2004, now Pat. No. 7,596,408, which is a continuation-in-part of application No. 10/730,873, filed on Dec. 9, 2003, now Pat. No. 7,242,982.

(60) Provisional application No. 60/431,854, filed on Dec. 9, 2002, provisional application No. 60/471,262, filed on May 16, 2003, provisional application No. 60/503,945, filed on Sep. 20, 2003, provisional application No. 60/503,946, filed on Sep. 20, 2003, provisional application No. 60/507,857, filed on Oct. 1, 2003.

(51) Int. Cl.
*A61N 1/02* (2006.01)

(52) U.S. Cl. .............................................. 607/36; 607/3
(58) Field of Classification Search .................. 607/1–3, 607/36–37, 45, 55–57, 136–137, 139; 604/890.1, 604/891.1, 502; 606/108, 129–130
See application file for complete search history.

(56) References Cited

U.S. PATENT DOCUMENTS

| 3,310,051 A | 3/1967 | Schulte |
| 3,522,811 A | 8/1970 | Schwartz et al. |

(Continued)

FOREIGN PATENT DOCUMENTS

DE    3940632    12/1990

(Continued)

OTHER PUBLICATIONS

Office Action from U.S. Appl. No. 11/735,826 dated Dec. 10, 2009 (10 pages).

(Continued)

*Primary Examiner* — Carl H Layno
*Assistant Examiner* — Jessica Sarcione
(74) *Attorney, Agent, or Firm* — Shumaker & Sieffert, P.A.

(57) ABSTRACT

An implantable medical device comprises an anti-infection agent. The implantable medical device may be configured for placement in the head of a patient and for monitoring or treatment of the brain. The implantable medical device may have a housing or it may have a housing and a member for providing a smooth interface between the device and the adjacent tissue. The anti-infection agent may be provided on or impregnated in the housing or the member. In some embodiments, the device includes a single module while in other embodiments a plurality of modules are coupled to provide a smaller profile. In some embodiments the implantable medical device may include both anti-infection and lubricious materials.

38 Claims, 18 Drawing Sheets

U.S. PATENT DOCUMENTS

| | | | |
|---|---|---|---|
| 3,690,325 A | 9/1972 | Kenny |
| 3,720,874 A | 3/1973 | Gorcik et al. |
| 3,724,467 A | 4/1973 | Avery et al. |
| 3,888,260 A | 6/1975 | Fischell |
| 3,913,587 A | 10/1975 | Newash |
| 3,926,198 A | 12/1975 | Kolenik |
| 3,941,135 A | 3/1976 | von Sturm et al. |
| 4,006,748 A | 2/1977 | Schulman |
| 4,010,760 A | 3/1977 | Kraska et al. |
| 4,013,081 A | 3/1977 | Kolenik |
| 4,040,412 A | 8/1977 | Sato |
| 4,094,321 A | 6/1978 | Muto |
| 4,256,115 A | 3/1981 | Bilitch |
| 4,266,552 A | 5/1981 | Dutcher et al. |
| 4,328,813 A | 5/1982 | Ray |
| 4,399,819 A | 8/1983 | Cowdery |
| 4,399,820 A | 8/1983 | Wirtzfeld et al. |
| 4,408,607 A | 10/1983 | Maurer |
| 4,499,907 A | 2/1985 | Kallok et al. |
| 4,503,860 A | 3/1985 | Sams et al. |
| 4,574,780 A | 3/1986 | Manders |
| 4,616,655 A | 10/1986 | Weinberg et al. |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A | 11/1990 | Owens et al. |
| 5,085,644 A | 2/1992 | Watson et al. |
| 5,116,345 A | 5/1992 | Jewell et al. |
| 5,144,946 A | 9/1992 | Weinberg et al. |
| 5,197,332 A | 3/1993 | Shennib |
| 5,207,218 A | 5/1993 | Carpentier et al. |
| 5,218,959 A | 6/1993 | Fenster |
| 5,220,929 A | 6/1993 | Marquit |
| 5,243,977 A | 9/1993 | Trabucco et al. |
| 5,252,090 A | 10/1993 | Giurtino et al. |
| 5,271,397 A | 12/1993 | Seligman et al. |
| 5,312,440 A | 5/1994 | Hirschberg et al. |
| 5,314,451 A | 5/1994 | Mulier |
| 5,314,453 A | 5/1994 | Jeutter |
| 5,396,813 A | 3/1995 | Takeuchi et al. |
| 5,411,538 A | 5/1995 | Lin |
| H1465 H | 7/1995 | Stokes |
| 5,431,695 A | 7/1995 | Wiklund et al. |
| 5,433,734 A | 7/1995 | Stokes et al. |
| 5,455,999 A | 10/1995 | Owens et al. |
| 5,456,698 A | 10/1995 | Byland et al. |
| 5,458,997 A | 10/1995 | Crespi et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,573,551 A | 11/1996 | Lin et al. |
| 5,613,935 A | 3/1997 | Jarvik |
| 5,638,832 A | 6/1997 | Singer et al. |
| 5,645,586 A | 7/1997 | Meltzer |
| 5,674,260 A | 10/1997 | Weinberg |
| 5,678,559 A | 10/1997 | Drakulic |
| 5,702,430 A | 12/1997 | Slimon et al. |
| 5,741,313 A | 4/1998 | Nason et al. |
| 5,755,743 A | 5/1998 | Volz et al. |
| 5,769,874 A | 6/1998 | Dahlberg |
| 5,776,169 A | 7/1998 | Schroeppel |
| 5,792,067 A | 8/1998 | Karell |
| 5,800,535 A | 9/1998 | Howard, III |
| 5,814,095 A | 9/1998 | Müller et al. |
| 5,836,935 A | 11/1998 | Ashton et al. |
| 5,843,150 A | 12/1998 | Adams et al. |
| 5,873,899 A | 2/1999 | Stutz, Jr. et al. |
| RE36,120 E | 3/1999 | Karell |
| 5,876,424 A | 3/1999 | O'Phelan et al. |
| 5,895,414 A | 4/1999 | Sanchez-Zambrano |
| 5,896,647 A | 4/1999 | Shkuratoff |
| 5,919,215 A | 7/1999 | Haeg et al. |
| 5,935,154 A | 8/1999 | Westlund |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,958,088 A | 9/1999 | Vu et al. |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,044,304 A | 3/2000 | Baudino |
| 6,061,593 A | 5/2000 | Fischell et al. |
| 6,067,474 A | 5/2000 | Schulman et al. |
| 6,091,979 A | 7/2000 | Madsen |
| 6,112,120 A | 8/2000 | Correas |
| 6,128,538 A | 10/2000 | Fischell et al. |
| 6,131,581 A | 10/2000 | Leysieffer et al. |
| 6,134,474 A | 10/2000 | Fischell et al. |
| 6,154,677 A | 11/2000 | Leysieffer |
| 6,162,487 A | 12/2000 | Darouiche |
| 6,168,580 B1 | 1/2001 | Yardley |
| 6,176,879 B1 | 1/2001 | Reischl et al. |
| 6,205,358 B1 | 3/2001 | Haeg et al. |
| 6,214,032 B1 | 4/2001 | Loeb et al. |
| 6,218,016 B1 | 4/2001 | Tedeschi et al. |
| 6,230,049 B1 | 5/2001 | Fischell et al. |
| 6,233,488 B1 | 5/2001 | Hess |
| 6,248,080 B1 | 6/2001 | Miesel et al. |
| 6,248,126 B1 | 6/2001 | Lesser et al. |
| 6,259,951 B1 | 7/2001 | Kuzma et al. |
| 6,263,225 B1 | 7/2001 | Howard, III |
| 6,266,556 B1 | 7/2001 | Ives et al. |
| 6,269,266 B1 | 7/2001 | Leysieffer |
| 6,272,382 B1 | 8/2001 | Faltys et al. |
| 6,283,997 B1 | 9/2001 | Garg et al. |
| 6,308,101 B1 | 10/2001 | Faltys et al. |
| 6,324,428 B1 | 11/2001 | Weinberg et al. |
| 6,324,433 B1 | 11/2001 | Errico |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,366,813 B1 | 4/2002 | DiLorenzo |
| 6,405,079 B1 | 6/2002 | Ansarinia |
| 6,415,184 B1 | 7/2002 | Ishikawa et al. |
| 6,427,086 B1 | 7/2002 | Fischell et al. |
| 6,436,422 B1 | 8/2002 | Trogolo et al. |
| 6,445,956 B1 | 9/2002 | Laird et al. |
| 6,456,256 B1 | 9/2002 | Amundson et al. |
| 6,456,886 B1 | 9/2002 | Howard et al. |
| 6,480,743 B1 | 11/2002 | Kirkpatrick et al. |
| 6,490,486 B1 | 12/2002 | Bradley |
| 6,498,951 B1 | 12/2002 | Larson et al. |
| 6,505,077 B1 | 1/2003 | Kast et al. |
| 6,516,227 B1 | 2/2003 | Meadows et al. |
| 6,516,808 B2 | 2/2003 | Schulman |
| 6,517,476 B1 | 2/2003 | Bedoya et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |
| 6,671,544 B2 | 12/2003 | Baudino |
| 6,726,678 B1 | 4/2004 | Nelson et al. |
| 6,736,770 B2 | 5/2004 | Leysieffer et al. |
| 6,782,292 B2 | 8/2004 | Whitehurst |
| 6,788,974 B2 | 9/2004 | Bardy et al. |
| 6,805,998 B2 | 10/2004 | Jenson et al. |
| 6,850,802 B2 | 2/2005 | Holsheimer |
| 6,882,881 B1 | 4/2005 | Lesser et al. |
| 6,899,976 B2 | 5/2005 | Larson et al. |
| 6,963,780 B2 | 11/2005 | Ruben et al. |
| 6,977,124 B2 | 12/2005 | Probst et al. |
| 6,994,933 B1 | 2/2006 | Bates |
| 7,010,351 B2 | 3/2006 | Firlik et al. |

| | | |
|---|---|---|
| 7,103,415 B2 | 9/2006 | Probst et al. |
| 7,107,097 B2 | 9/2006 | Stern et al. |
| 7,110,819 B1 | 9/2006 | O'Hara |
| 7,212,864 B2 | 5/2007 | Wahlstrand et al. |
| 7,242,982 B2 | 7/2007 | Singhal et al. |
| 7,263,401 B2 | 8/2007 | Scott et al. |
| 7,454,251 B2 | 11/2008 | Rezai et al. |
| 7,596,399 B2 | 9/2009 | Singhal et al. |
| 7,596,408 B2 | 9/2009 | Wahlstrand et al. |
| 7,702,380 B1 | 4/2010 | Dean |
| 2001/0033953 A1 | 10/2001 | Takeuchi et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0042630 A1 | 4/2002 | Bardy et al. |
| 2002/0042634 A1 | 4/2002 | Bardy et al. |
| 2002/0051550 A1 | 5/2002 | Leysieffer |
| 2002/0059049 A1 | 5/2002 | Bradbury et al. |
| 2002/0068958 A1 | 6/2002 | Bardy et al. |
| 2002/0072770 A1 | 6/2002 | Pless |
| 2002/0077670 A1 | 6/2002 | Archer et al. |
| 2002/0087201 A1 | 7/2002 | Firlik et al. |
| 2002/0099412 A1 | 7/2002 | Fischell et al. |
| 2002/0103510 A1 | 8/2002 | Bardy et al. |
| 2002/0107546 A1 | 8/2002 | Ostroff et al. |
| 2002/0147498 A1 | 10/2002 | Tallarida et al. |
| 2002/0161403 A1 | 10/2002 | Meadows et al. |
| 2002/0165588 A1 | 11/2002 | Fraley et al. |
| 2002/0169485 A1 | 11/2002 | Pless et al. |
| 2002/0177882 A1 | 11/2002 | DiLorenzo |
| 2003/0004428 A1 | 1/2003 | Pless et al. |
| 2003/0004546 A1 | 1/2003 | Casey |
| 2003/0017372 A1 | 1/2003 | Probst et al. |
| 2003/0040781 A1 | 2/2003 | Larson et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0091893 A1 | 5/2003 | Kishiyama et al. |
| 2003/0109903 A1 | 6/2003 | Berrang et al. |
| 2003/0120320 A1 | 6/2003 | Solom |
| 2003/0125786 A1 | 7/2003 | Gliner et al. |
| 2003/0130706 A1 | 7/2003 | Sheffield et al. |
| 2003/0171787 A1 | 9/2003 | Money et al. |
| 2003/0204229 A1 | 10/2003 | Stokes |
| 2004/0015070 A1 | 1/2004 | Liang et al. |
| 2004/0030245 A1 | 2/2004 | Noble et al. |
| 2004/0082977 A1 | 4/2004 | Engmark et al. |
| 2004/0102828 A1 | 5/2004 | Lowry et al. |
| 2004/0172090 A1 | 9/2004 | Janzig et al. |
| 2004/0173221 A1 | 9/2004 | Singhal et al. |
| 2004/0176673 A1 | 9/2004 | Wahlstrand et al. |
| 2004/0176750 A1 | 9/2004 | Nelson et al. |
| 2004/0176815 A1 | 9/2004 | Janzig et al. |
| 2004/0176816 A1 | 9/2004 | Singhal et al. |
| 2004/0176817 A1 | 9/2004 | Wahlstrand et al. |
| 2004/0176818 A1 | 9/2004 | Wahlstrand et al. |
| 2004/0176819 A1 | 9/2004 | Wahlstrand et al. |
| 2004/0181263 A1 | 9/2004 | Balzer et al. |
| 2004/0186528 A1 | 9/2004 | Ries et al. |
| 2004/0243481 A1 | 12/2004 | Bradbury et al. |
| 2005/0003268 A1 | 1/2005 | Scott et al. |
| 2005/0004618 A1 | 1/2005 | Scott et al. |
| 2005/0004619 A1 | 1/2005 | Wahlstrand et al. |
| 2005/0004620 A1 | 1/2005 | Singhal et al. |
| 2005/0004637 A1 | 1/2005 | Singhal et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0245806 A1 | 11/2005 | Singhal et al. |
| 2005/0245984 A1 | 11/2005 | Singhal et al. |
| 2006/0116743 A1 | 6/2006 | Gibson et al. |
| 2006/0129205 A1 | 6/2006 | Boveja et al. |
| 2006/0149336 A1 | 7/2006 | Meadows |
| 2006/0184210 A1 | 8/2006 | Singhal et al. |
| 2006/0184220 A1 | 8/2006 | Singhal et al. |
| 2006/0195156 A1 | 8/2006 | Singhal et al. |
| 2007/0074732 A1 | 4/2007 | Singhal et al. |
| 2007/0185539 A1 | 8/2007 | Singhal et al. |
| 2007/0255338 A1 | 11/2007 | Wahlstrand et al. |
| 2008/0021511 A1 | 1/2008 | Scott et al. |
| 2008/0065173 A1 | 3/2008 | Wahlstrand et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |

FOREIGN PATENT DOCUMENTS

| | | |
|---|---|---|
| EP | 1 145 735 A2 | 10/2001 |
| EP | 1 145 736 A2 | 10/2001 |
| GB | 1 161 579 | 8/1969 |
| WO | WO 92/20402 | 11/1992 |
| WO | WO 99/06108 | 2/1999 |
| WO | WO 99/34758 | 7/1999 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | WO 2004/052458 | 6/2004 |
| WO | WO 2004/052459 | 6/2004 |

OTHER PUBLICATIONS

Amendment from U.S. Appl. No. 11/735,828, filed Mar. 9, 2010 (23 pages).
Office Action from U.S. Appl. No. 11/735,826 dated Apr. 6, 2011 (11 pages).
Response to Office Action from U.S. Appl. No. 11/735,826, filed Jul. 6, 2011 (25 pages).
Notification of Transmittal of the International Search Report and the Written Opinion of the International Searching Authority dated Dec. 10, 2004, International Application No. PCT/US2004/022109.
Notification of Transmittal of the International Search Report dated May 7, 2004, International Application No. PCT/US03/38928.
Written Opinion dated Dec. 16, 2004, International Application No. PCT/US03/38928.
Notification of Transmittal of the International Preliminary Examination Report dated Apr. 11, 2005, International Application No. PCT/US03/38928.
U.S. Appl. No. 12/538,623, filed Aug. 10, 2009, entitled "Implantation of Implantable Medical Device," by Singhal et al.
U.S. Appl. No. 12/538,617, filed Aug. 10, 2009, entitled "Implantation of Implantable Medical Device," by Singhal et al.
U.S. Appl. No. 12/538,605, filed Aug. 10, 2009, entitled "Implantation of Implantable Medical Device," by Singhal et al.
U.S. Appl. No. 12/609,957, filed Oct. 30, 2009, entitled "Non-Hermetic Direct Current Interconnect," by Wahlstrand et al.
"Surgical Process," Animation Screenshots from http://www.cochlearamerica.com/800.asp, 7 pgs. (2002).
"Candidates Brochure," http://www.cochlearamerica.com/pdfs/candidatebrochglobal.pdf, 14 pgs. (Aug. 19, 2002).
"Research and Development," http://www.cochlearamericas.com/384.asp, 1 pg. (last printed Feb. 3, 2004).
"The World Leader in cochlear implants—revolutionizing hearing for adults and infants," http://www.cochlear.com, 1 pg. (last printed Feb. 3, 2004).
"Cochlear: innovator of the Nucleus 3 cochlear implant system," http://www.cochlearamericas.com, 1 pg. (last printed Feb. 3, 2004).
"What is a Cochlear Implant," http://www.cochlearamericas.com/What/161.asp, 1 pg. (last printed Feb. 3, 2004).
"ESPrit 3G Speech Processor," http://www.cochlearamericas.com/591.asp, 2 pgs. (last printed Feb. 3, 2004).

"Nucleus 3 System," http://www.cochlearamericas.com/Products/465.asp, 1 pg. (last printed Feb. 3, 2004).

"Internal Components: Nucleus 24 Cochlear Implants," http://www.cochlearamericas.com/374.asp, 1 pg. (last printed Feb. 3, 2004).

"Nucleus 24 Contour," http://www.cochlearamericas.com/568.asp, 2 pgs. (last printed Feb. 3, 2004).

"Nucleus 24 M," http://www.cochlearamericas.com/372.asp, 1 pg. (last printed Feb. 3, 2004).

"Nucleus 24 K," http://www.cochlearamericas.com/371.asp, (last printed Feb. 3, 2004).

"Nucleus 24 Double Array," http://www.cochlearamericas.com/370.asp, 1 pg. (last printed Feb. 3, 2004).

"Nucleus 24 ABI: Auditory Brainstem Implant," http://www.cochlearamericas.com/373.asp, 2 pgs. (last printed Feb. 3, 2004).

"Nucleus Speech Processors," http://www.cochlearamericas.com/629.asp, 1 pg. (last printed Feb. 3, 2004).

"Spring: body worn speech processor," http://www.cochlearamericas.com/1010.asp, 1 pg. (last printed Feb. 3, 2004).

"Cochlear," http://www.cochlearamericas.com/Recipients/978.asp, 3 pgs. (last printed Feb. 3, 2004).

Notification of the International Preliminary Report on Patentability for International Application No. PCT/US2004/022109, filed Jul. 12, 2004, 11 pgs. (Sep. 6, 2005).

Answers.com, www.answers.com, defined: discrete components, accessed on Mar. 2, 2007 (2 pages).

Office Action dated Aug. 5, 2008 for U.S. Appl. No. 10/731,867 (12 pgs.).

Reponsive Amendment dated Nov. 5, 2008 for U.S. Appl. No. 10/731,867 (15 pgs.).

European Communication from corresponding European Application No. 03 796 790.8-2305 mailed Jun. 19, 2009 (5 pages).

IMPLANTABLE MEDICAL DEVICE WITH ANTI-INFECTION AGENT

This is a continuation of U.S. patent application Ser. No. 10/837,319 by Singhal et al., which was filed on Apr. 30, 2004 and published on Jan. 6, 2005 as U.S. Patent Application Publication No. 2005/0004620 and issued as U.S. Pat. No. 7,596,408 on Sep. 29, 2009, and is entitled, "IMPLANTABLE MEDICAL DEVICE WITH ANTI-INFECTION COATING." U.S. patent application Ser. No. 10/837,319 is a continuation-in-part of U.S. patent application Ser. No. 10/730,873, filed Dec. 9, 2003, which issued as U.S. Pat. No. 7,242,982 to Singhal et al. on Jul. 20, 2007, is entitled "OVERMOLD FOR A MODULAR IMPLANTABLE MEDICAL DEVICE," and in turn claims the benefit of:

a. U.S. Provisional Application Serial No. 60/431,854, filed on Dec. 9, 2002, entitled "CRANIAL NEUROSTIMULATOR AND METHOD," by Skime et al.;
b. U.S. Provisional Application Serial No. 60/471,262, filed on May 16, 2003, entitled "IMPLANTABLE CRANIAL MEDICAL DEVICES AND METHODS," by Wahlstrand et al.;
c. U.S. Provisional Application Serial No. 60/503,945, filed on Sep 20, 2003, entitled "IMPLANTABLE CRANIAL MEDICAL DEVICES AND METHODS," by Wahlstrand et al.;
d. U.S. Provisional Application Serial No. 60/503,946, filed on Sep. 20, 2003, entitled "IMPLANTABLE CRANIAL MEDICAL DEVICES AND METHODS," by Wahlstrand et al.; and
e. U.S. Provisional Application Serial No. 60/507,857, filed on Oct. 1, 2003, entitled "THIN NEURO STIMULATION SYSTEM, DEVICE AND METHOD," by Wahlstrand et al.

Each of the preceding applications is incorporated herein by reference in its entirety.

The following commonly-assigned U.S. patents and patent applications are also incorporated herein by reference:

1. U.S. Patent Application Publication No. 2004/0176818 by Wahlstrand et al., which was filed on Dec. 9, 2003 and published on Sep. 9, 2004, and is entitled "MODULAR IMPLANTABLE MEDICAL DEVICE";
2. U.S. Patent Application Publication No. 2004/0173221 by Singhal et al., which was filed on Dec. 9, 2003 and published on Sep. 9, 2004, and is entitled "IMPLANTATION OF LOW-PROFILE IMPLANTABLE MEDICAL DEVICE";
3. U.S. Pat. No. 7,392,089 to Wahlstrand et al., which issued on Jun. 24, 2008 and is entitled "REDUCING RELATIVE INTERMODULE MOTION IN A MODULAR IMPLANTABLE MEDICAL DEVICE";
4. U.S. Pat. No. 7,848,817 to Janzig et al., which was filed on Dec. 9, 2003 and issued on Dec. 7, 2010, and is entitled "COUPLING MODULE OF A MODULAR IMPLANTABLE MEDICAL DEVICE";
5. U.S. Patent Application Publication No. 2004/0176815 by Janzig et al., which was filed on Dec. 9, 2003 and published on Sep. 9, 2004, and is entitled "LOW-PROFILE IMPLANTABLE MEDICAL DEVICE";
6. U.S. Pat. No. 7,529,586 to Wahlstrand et al., which issued on May 5, 2009 and is entitled "CONCAVITY OF AN IMPLANTABLE MEDICAL DEVICE";
7. U.S. Patent Application Publication No. 2004/0176816 by Singhal et al., which was filed on Dec. 9, 2003 and published on Sep. 9, 2004, and is entitled "LEAD CONNECTION MODULE OF A MODULAR IMPLANTABLE MEDICAL DEVICE";
8. U.S. Pat. No. 7,212,864 to Wahlstrand et al., which issued on May 1, 2007 and is entitled "MODULAR IMPLANTABLE MEDICAL DEVICE";
9. U.S. Pat. No. 7,263,401 to Wahlstrand et al., which issued on Aug. 28, 2007 and is entitled "IMPLANTABLE MEDICAL DEVICE WITH A NONHERMETIC BATTERY";
10. U.S. Patent Application Publication No. 2005/0004637 by Singhal et al., which was filed on Apr. 29, 2004 and published on Jan. 6, 2005, and is entitled "EXPLANTATION OF IMPLANTABLE MEDICAL DEVICE";
11. U.S. Patent Application Publication No. 2005/0245806 by Singhal et al., which was filed on Apr. 29, 2004 and published on Nov. 3, 2005, and is entitled "IMPLANTATION OF IMPLANTABLE MEDICAL DEVICE";
12. U.S. Pat. No. 7,317,947 to Wahlstrand et al., which is entitled "HEADSET RECHARGER FOR CRANIALLY IMPLANTABLE MEDICAL DEVICE" and issued on Jan. 8, 2008; and
13. U.S. Patent Application Publication No. 2005/0003268 by Scott et al., which was filed on Apr. 29, 2004 and published on Jan. 6, 2005, and is entitled "BATTERY HOUSING CONFIGURATION."

TECHNICAL FIELD

The invention relates to medical devices, and more particularly, to implantable medical devices that deliver therapy to and/or monitor a patient.

BACKGROUND

Implantable medical devices (IMD's) carry the risk of causing infection in the patient. Bacteria on the surface of the IMD can result in serious patient problems.

It is desirable to implant IMD's near the site of treatment (e.g., in the head when the IMD is a brain stimulator). These remote locations often provide spaces that are either small or shaped in such a way that traditional IMD's do not fit therein or for which it is desirable to create a smooth interface with the surrounding tissue. Different configurations of IMD's may be devised to better fit into these spaces. However, these different configurations raise questions about the possibility of increased infection.

SUMMARY

In general, the invention relates to an implantable medical device including an anti-infection agent on the external surface or impregnated in the external surface for reducing the likelihood of infection.

Various embodiments of the invention are presented including a device for implantation in the head of a patient. Some more specific embodiments configure the device for implantation between the cranium and the scalp.

Various embodiments also include a member coupled to the module or modules for providing a smooth interface between the device and adjacent tissue. An anti-infection agent is on or impregnated in the member.

Various other embodiments also include a member coupled to the module or modules for providing a smooth interface between the device and the scalp or the tissue near the scalp. These embodiments include an anti-infection agent on or impregnated in the member. The member may be any material capable of providing a smooth interface with the tissue. The member can include elastomeric materials, such as silicone, and/or non-elastomeric materials such as polysulfone and polyurethane.

Various embodiments of the invention include a single module while other embodiments include a plurality of interconnected modules. These embodiments include an anti-infection agent on or impregnated in the housing or member.

Other embodiments include an implantable medical device including a lubricious material and an anti-infection agent. Methods of fabricating an implantable medical device including an anti-infection agent are also presented.

The details of one or more embodiments of the invention are set forth in the accompanying drawings and the description below. Other embodiments of the invention will be apparent from the description and drawings, and from the claims.

DETAILED DESCRIPTION

Figure 1A:
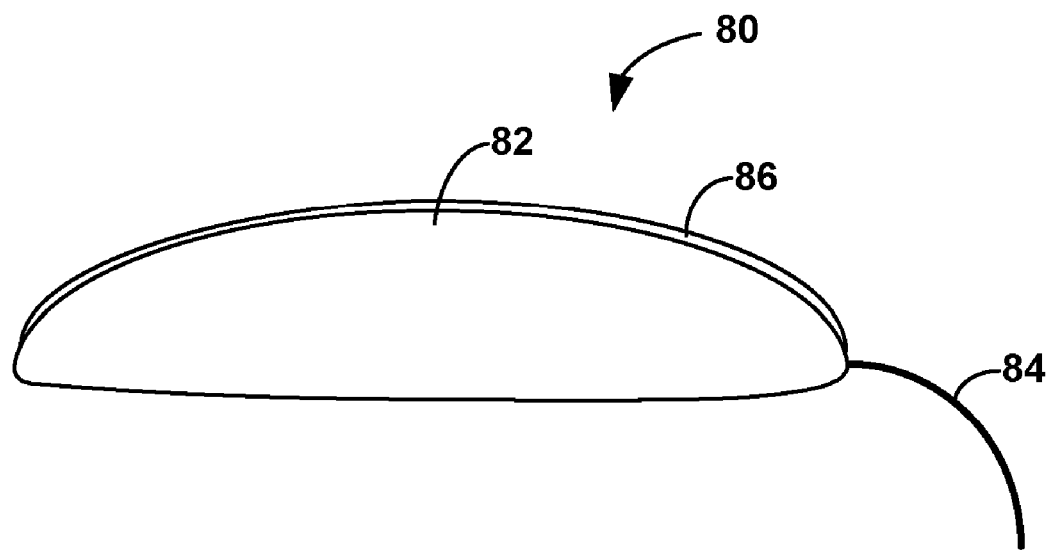
FIG. 1A is a conceptual diagram illustrating one embodiment of an implantable medical device of the present invention.

FIG. 1A is a conceptual diagram of an implantable medical device 80 including housing 82 and therapy delivery element 84 (e.g., lead, catheter, extension and lead). An anti-infection agent and/or lubricious material as described herein, may be disposed on or impregnated in at least a portion of the implantable medical device 80. In one embodiment the anti-infection agent and/or lubricious material may be placed on the housing 82 in the form of a coating 86. Disposing an anti-infection agent and/or lubricious material on or impregnated in the device 80 may facilitate insertion of the device 80 into the implantable location within a human body. The anti-infection agent reduces the likelihood of infection. The lubricious material reduces friction between the device 80 and the tissue near the device 80. In cases where the implantable medical device is implanted in a tight space such as between the cranium and the scalp, the lubricious material may reduce the likelihood of skin erosion by decreasing the friction forces between the device and the scalp. A lubricious material may also minimize fibrous capsule growth around the device by lowering the friction between the device and the scalp. This would have the additional benefit of reducing the likelihood of infection.

For many therapies such as brain stimulation for movement disorders it may be desirable for the device to provide unipolar stimulation whereby the housing is used as an electrode. Therefore, in some embodiments it may be desirable to use a lubricious material that is electrically conductive or to apply the lubricious material to less than the entire housing.

In one embodiment, housing 82 includes at least a portion of the electronics for providing monitoring of or therapy to a patient. Some examples of implantable medical devices that include at least a portion of the electronics for providing monitoring of or therapy to a patient include implantable neurostimulators, implantable drug delivery pumps, pacemakers, defibrillators and monitoring devices that receive physiological signals from a patient and store or relay such information. Such devices that provide therapy to the patient may be open or closed loop devices (e.g., closed loop device receives sensed information and delivers therapy based on the sensed information).

Application of an anti-infection agent and/or lubricious material is also desirable in the case of a modular device having more than one module and housing. In such a case a one embodiment includes an anti-infection agent and/or lubricious material on at least a portion of both housings.

An implantable medical device may be implantable anywhere in the body. For example, the implantable medical device may be implanted in the abdomen, pectoral or buttock areas. An implantable medical device may also be implanted in the head of a patient such as between the cranium and the scalp. Other embodiments may include an implantable medical device for implantation partially or wholly within a groove or recess placed in the cranium.

Figure 1B:
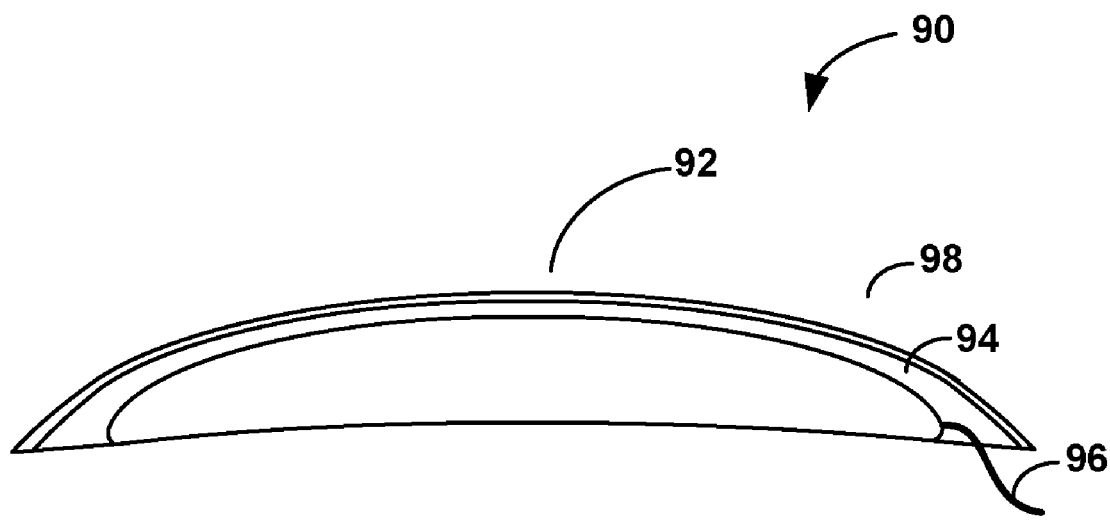
FIG. 1B is a conceptual diagram illustrating another embodiment of an implantable medical device of the present invention.

As shown in FIG. 1B, an implantable medical device may be an implantable medical device 90 for implantation in the head of a patient. Device 90 may be placed between the cranium and the scalp. Device 90 includes housing 92, member 94 and therapy delivery element 96. Member 94 provides a substantially smooth interface between device 90 and the scalp or other tissue near the scalp. In one sub-embodiment of this embodiment, the member 94 partially encapsulates housing 92. An anti-infection agent and/or lubricious material may be disposed on or impregnated in the member 94. In one embodiment, the anti-infection agent and/or lubricious material is provided as a coating 98 on the member 94. In one embodiment the anti-infection agent and/or lubricious material 98 is only on the convex side of the member 94. Application of the lubricious material 98 to the convex side of the member 94 is desired to reduce friction between the convex side of the member 94 and the scalp or other tissue near the scalp. However, the lubricious material may also be applied to more than one side of the member 94. Application of the anti-infection agent may be over all or a part of the device. In a cranial application it may be desirable to apply the anti-infection agent to the concave side of the device or member.

Figure 1C:
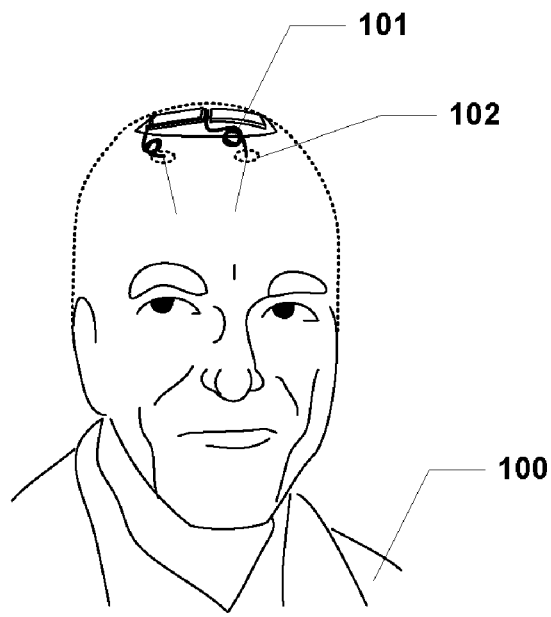
FIGS. 1C and 1D are conceptual diagrams illustrating a modular implantable medical device implanted in a patient according to an example embodiment of the present invention.
Figure 1D:
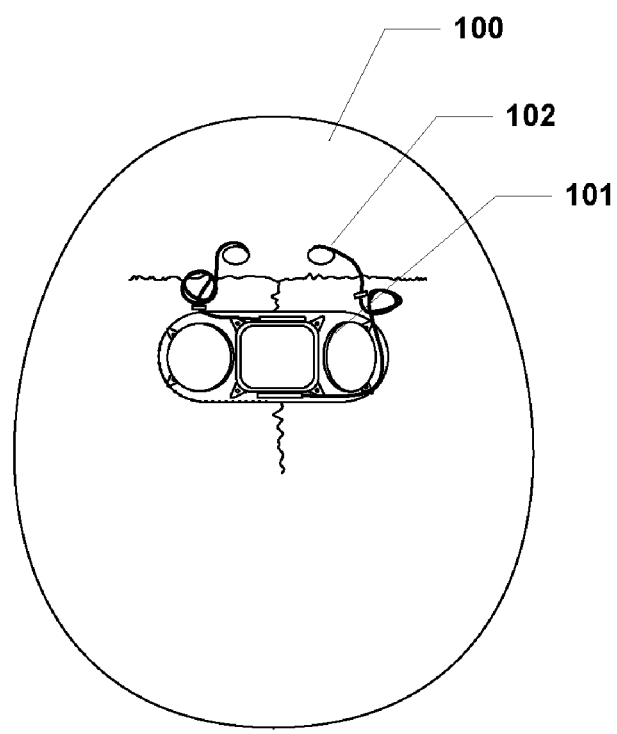

In another embodiment the implantable medical device may be a modular implantable medical device. FIGS. 1C and 1D are conceptual diagrams illustrating a modular implantable medical device 101 implanted within a patient 100. By constructing modular implantable medical device 101 as a set of distributed modules connected together as described herein, modular implantable medical device 101 may be implanted at locations for which implantation of conventional implantable medical devices has been deemed undesirable, thus permitting the implantable medical device 101 to be implanted near a monitoring and/or therapy delivery location. In the example illustrated within FIGS. 1C-1D, modular implantable medical device 101 is implanted under the scalp of the patient 100 in order to locate the device 101 close to the location to which therapy is to be delivered via leads 102, i.e., the brain of patient 100. The low profile and the shape of modular implantable medical device 101 as described herein can reduce the risk of infection and skin erosion associated with implantation of matter beneath the scalp, and may provide a cosmetically acceptable profile when implanted beneath the scalp.

Modular implantable medical device 101 may deliver stimulation to the brain of patient 100 to, for example, provide deep brain stimulation (DBS) therapy, or to stimulate the cortex of the brain. Cortical stimulation may involve stimulation of the motor cortex. Modular implantable medical device 101 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular implantable medical device 101 is not limited to delivery of stimulation to the brain of patient 100, and may be employed with leads 102 deployed anywhere in the head or neck including, for example, leads deployed on or near the surface of the cranium, leads deployed beneath the cranium such as near or on the dura mater, leads placed adjacent cranial or other nerves in the neck or head, or leads placed directly on the surface of the brain. Moreover, modular implantable medical device 101 is not limited to implantation under the scalp of patient 100. Indeed, modular implantable medical device 101 may be implanted anywhere within patient 100. For example, modular implantable medical device 101 can be implanted within the neck of patient 100, and deliver stimulation to the vagus nerve or the cervical region of the spinal cord.

Modular implantable medical device 101 may alternatively be implanted within a pectoral region or the abdomen of patient 100 to act as a diaphragmatic pacer, or to provide any of the monitoring and therapy delivery functions known in the art to be associated with cardiac pacemakers. Further, modular implantable medical device 101 may be implanted in the upper buttock region and deliver spinal cord, urological or gastrological stimulation therapy, or may be configured to be implanted within the periphery, e.g., limbs, of patient 100 for delivery of stimulation to the muscles and/or peripheral nervous system of patient 100. As is the case with cranial implantation, the modularity of implantable medical device 101 may enable implantation at some of these example locations for which implantation of conventional implantable medical devices is generally deemed undesirable.

Modular implantable medical device 101 is not limited to embodiments that deliver stimulation. For example, in some embodiments modular implantable medical device 101 may additionally or alternatively monitor one or more physiological parameters and/or the activity of patient 100, and may include sensors for these purposes. Where a therapy is delivered, modular implantable medical device 101 may operate in an open loop mode (also referred to as non-responsive operation), or in a closed loop mode (also referred to as responsive). Modular implantable medical device 101 may also provide warnings based on the monitoring.

As discussed above, the ability of a modular implantable medical device 101 according to the invention to be implanted close to a region within patient 100 to be monitored enables the use of shorter leads 102. Shorter leads 102 may advantageously improve the accuracy of such sensors by reducing noise attributable to leads 102. Shorter leads 102 may also advantageously reduce the negative affects of imaging techniques such as magnetic resonance imaging "MRI" on a person implanted with implantable medical device 101.

Additional alternate embodiments for implantable medical devices implemented according to principles of the present invention may also include non-electrical based therapies such as targeted introduction of fluids and similar therapeutic materials using pumps and reservoirs of material. One skilled in the art will recognize that any number of implantable devices may be possible without deviating from the spirit and scope of the present invention as recited within the attached claims.

Figure 2:
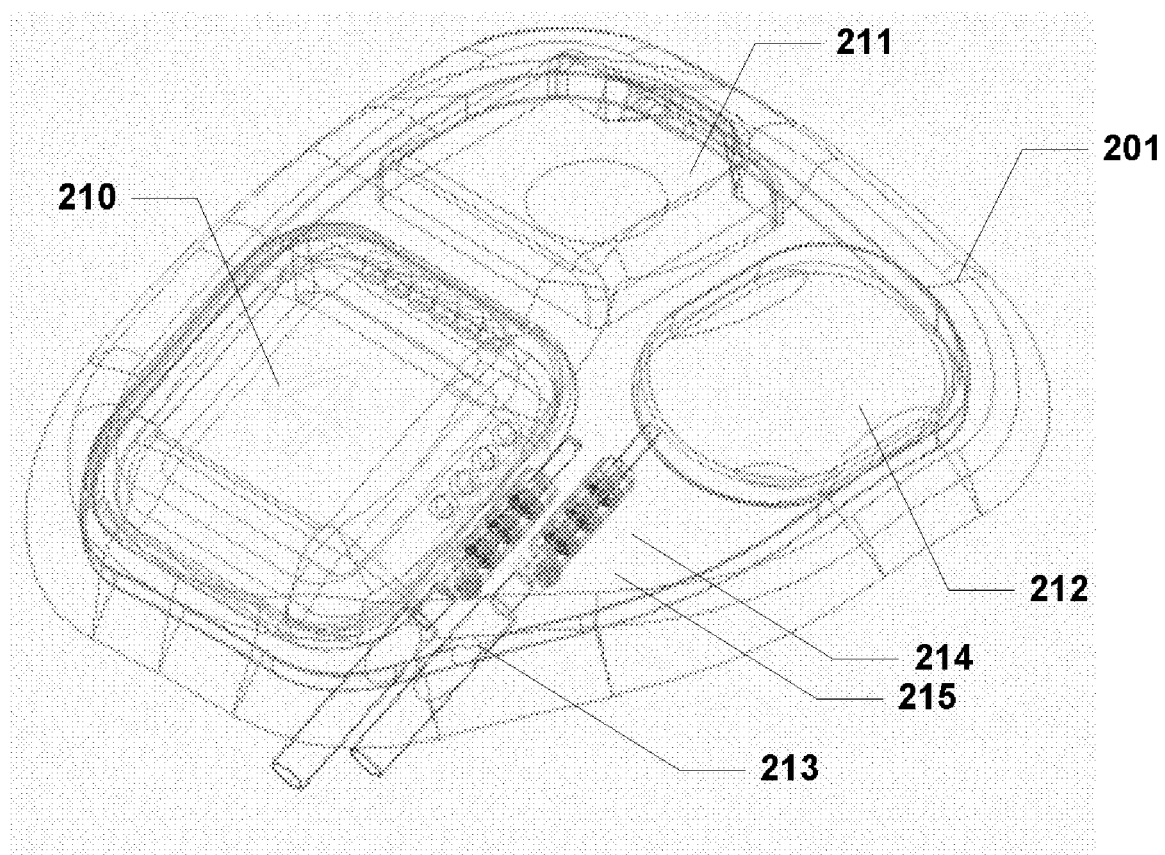
FIG. 2 is a schematic diagram illustrating a modular implantable medical device according to another embodiment of the present invention.

FIG. 2 is a schematic diagram illustrating a modular implantable medical device 201 according to another embodiment of the present invention. In this example embodiment, implantable medical device 201 is arranged in a triangular configuration. Modular implantable medical device 201 includes three modules: a control module 210, a power source module 211, and a recharge module 212. Each of modules 210-212 includes a respective housing. Modular implantable medical device 201 also contains a set of lead connection modules 213 that permits external leads 102 (FIGS. 1C and 1D) to be connected to control module 210 as needed. In this way, lead connection module 213 is configured to receive external leads 102 that are separate from lead connection module 213. The distribution of functional components of modular implantable medical device 201 into modules permits modular implantable medical device 201 to possess a thin profile by spreading the components over a larger surface area.

Control module 210 includes control electronics for controlling the monitoring and/or therapy delivery functions of modular implantable medical device 201, such as a microprocessor, and may include therapy delivery circuitry. Power source module 211 includes a power source that provides energy to control module 210, which in some embodiments is a rechargeable power source such as a rechargeable battery and/or capacitor. Recharge module 212 includes a recharge coil for inductively receiving energy to recharge a rechargeable power source within power source module 211.

In some embodiments, one or modules may be coupled by coupling modules (not shown). A coupling module may be flexible, and may include a lumen to carry a conductor or a fluid between modules of a modular implantable medical device. In some embodiments, a coupling module is made of a flexible material such as silicone or a flexible polymer. In other embodiments a coupling module is hermetic and made of substantially less flexible material, such as titanium or stainless steel, and the flexibility of a coupling module is provided by the configuration and/or construction the coupling module.

A coupling module may be flexible in a plurality of directions to provide modules of a modular implantable medical device with multiple degrees of freedom of motion with respect to each other. In exemplary embodiments, a coupling module provides at least three degrees of motion, and the degrees of motion provided include rotational motion.

Additional details regarding modules 210, 211 and 212, additional or alternative modules for a modular implantable medical device, the interconnection of modules within a modular implantable medical device, and lead connection modules 213 may be found in commonly assigned U.S. Patent Application Publication No. 2004/0176818 by Wahlstrand et al., entitled "MODULAR IMPLANTABLE MEDICAL DEVICE"; commonly assigned U.S. Pat. No. 7,848,817 to Janzig et al., entitled "COUPLING MODULE OF A MODULAR IMPLANTABLE MEDICAL DEVICE"; and commonly assigned U.S. Patent Application Publication No. 2004/0176816 by Singhal et al., entitled "LEAD CONNECTION MODULE OF A MODULAR IMPLANTABLE MEDICAL DEVICE." As illustrated in FIG. 2, modular implantable medical device 201 includes a member 214. A member generally serves as a smooth interface between one or more modules and the body tissue.

A member may be made of any material. In one embodiment the member may be made of a metal. For example, a member may be made of titanium or of other biocompatible metals. In another embodiment, the member may be made of a soft, biocompatible material. In other embodiments the member may be made of multiple materials. An anti-infection agent and/or lubricious material 215 may be on or impregnated in a portion of the member 214 (for example, on the convex side of the member 214). Alternatively, the anti-infection agent and/or lubricious material 215 may be on or impregnated in the entire outer surface of the member 214.

Member 214 at least partially encapsulates modules 210-212. Further, as will be described in greater detail below, lead connection modules 213 may be formed in member 214. Member may integrate modules 210-212 into a structure. Member 214 may provide a flexible structure that permits the device 501 to conform to a variety of implant locations.

In some embodiments, member 214 may be curved to match the shape of the location within a patient in which the device is being implanted. For example, implantation of modular implantable medical device 201 under the scalp of a patient may be accomplished if member 214 is concave (as viewed from the cranium) to substantially conform to the shape of the cranium of the patient and convex (as viewed from the scalp) to provide a smooth interface with the scalp or tissue near the scalp and thus reduces the likelihood of skin erosion and other problems associated with edges or protrusions pushing against the scalp. Concavity of modular implantable medical devices is described in greater detail in a commonly-assigned U.S. Pat. No. 7,529,586 to Wahlstrand et al., entitled "CONCAVITY OF AN IMPLANTABLE MEDICAL DEVICE." Any number of shapes may be used to match a particular implantable medical device 201 to an implantation location for a device.

Member 214 may comprise a solid biocompatible elastomeric material that is soft and flexible such as silicone. In some embodiments, member 214 comprises two or more materials, and two or more components. For example, member may comprise one or more elastomeric components formed of an elastomeric material, such as silicone, and one or more non-elastomeric components formed of a non-elastomeric material, such as polysulfone, or a polyurethane such as Tecothane®, which is commercially available from Hermedics Polymer Products, Wilmington, Mass. The one or more elastomeric components may provide the overall shape and flexibility of modular implantable medical device 201, while the non-elastomeric components may provide structural integrity for modular implantable medical device 201, restrict intermodule motion within modular implantable medical device 201 to certain ranges, and form a part of the lead interconnection modules 213. Further detail regarding reduction of intermodule motion within modular implantable medical devices may be found in a commonly-assigned U.S. Pat. No. 7,392,089 to Wahlstrand et al., entitled "REDUCING RELATIVE INTERMODULE MOTION IN A MODULAR IMPLANTABLE MEDICAL DEVICE."

FIGS. 3A-3F are schematic diagrams illustrating various arrangements of multiple modules within a modular implantable medical device 301 according to various embodiments of the present invention. In each of these embodiments, modular implantable medical device 301 has three modules as discussed above in reference to FIG. 2: a control module 210, a power source module 211, and a recharge module 212. These modules may be arranged into a variety of configurations, including those illustrated, as long as any required interconnections needed between the modules, e.g., coupling modules, may be routed within the device. The various embodiments include triangular configurations, in such as those shown in FIGS. 3A-C, and inline configurations, such as those shown in FIGS. 3D-F. The set of lead connection devices 313 may be located in various locations within the device as well.

Figure 3A:
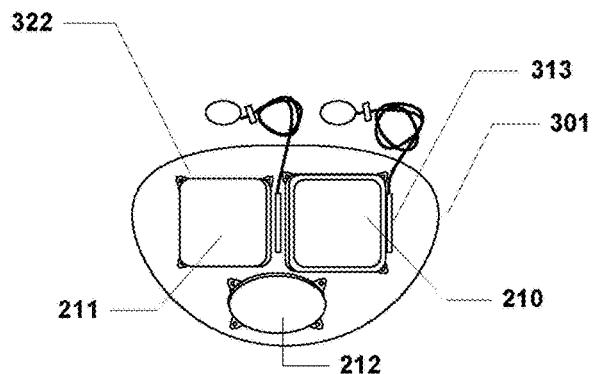
FIGS. 3A-3F are schematic diagrams illustrating various arrangements of modules within a modular implantable medical device according to various embodiments of the present invention.
Figure 3B:
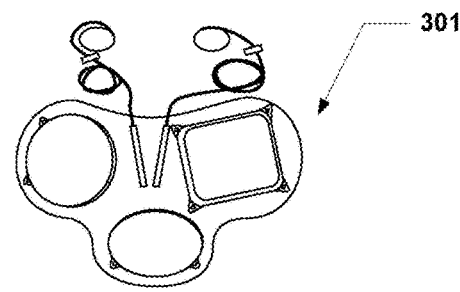
Figure 3C:
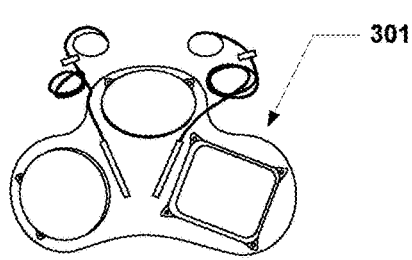
Figure 3D:
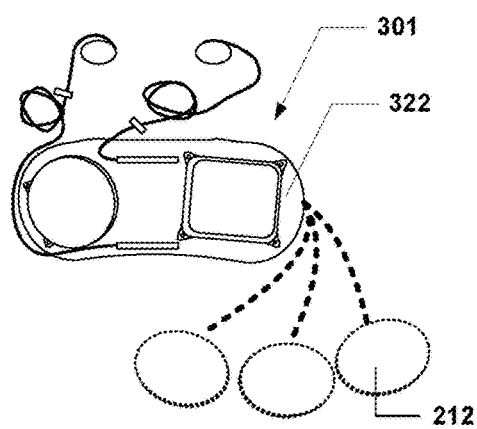
Figure 3E:
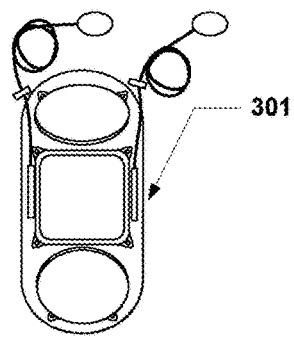
Figure 3F:
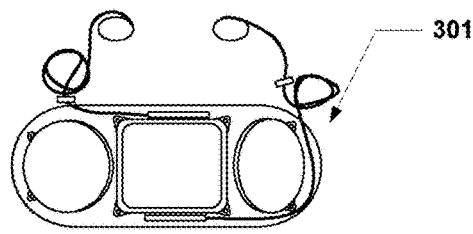

In some embodiments, such as those illustrated in FIGS. 3A-C and 3E-F, a member 322 at least partially encapsulates each of modules 210, 211 and 212. In other embodiments, such as that illustrated in FIG. 3D, at least one of the modules of modular IMD 301 is located outside of member 322. Module 212 located outside of member may, as shown in FIG. 3D, be tethered to member 322, allowing module 212 to be freely positioned some significant distance from member 322. Additional details relating to configurations of modules within a modular implantable medical devices and tethering of modules of an implantable medical device may be found in U.S. Patent Application Publication No. 2004/0176818 by Wahlstrand et al., entitled "MODULAR IMPLANTABLE MEDICAL DEVICE."

Figure 4A:
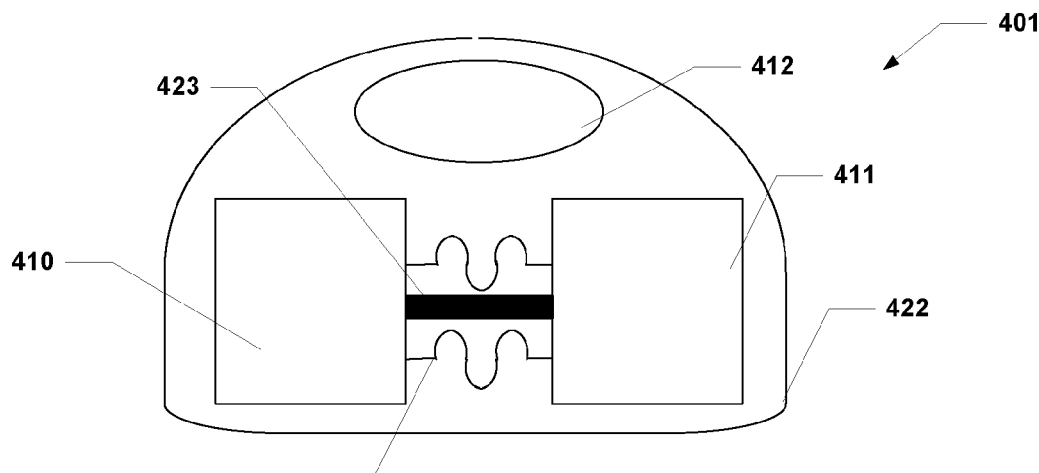
FIGS. 4A-4C are schematic diagrams illustrating the construction of a member of a modular implantable medical device according to the present invention.
Figure 4B:
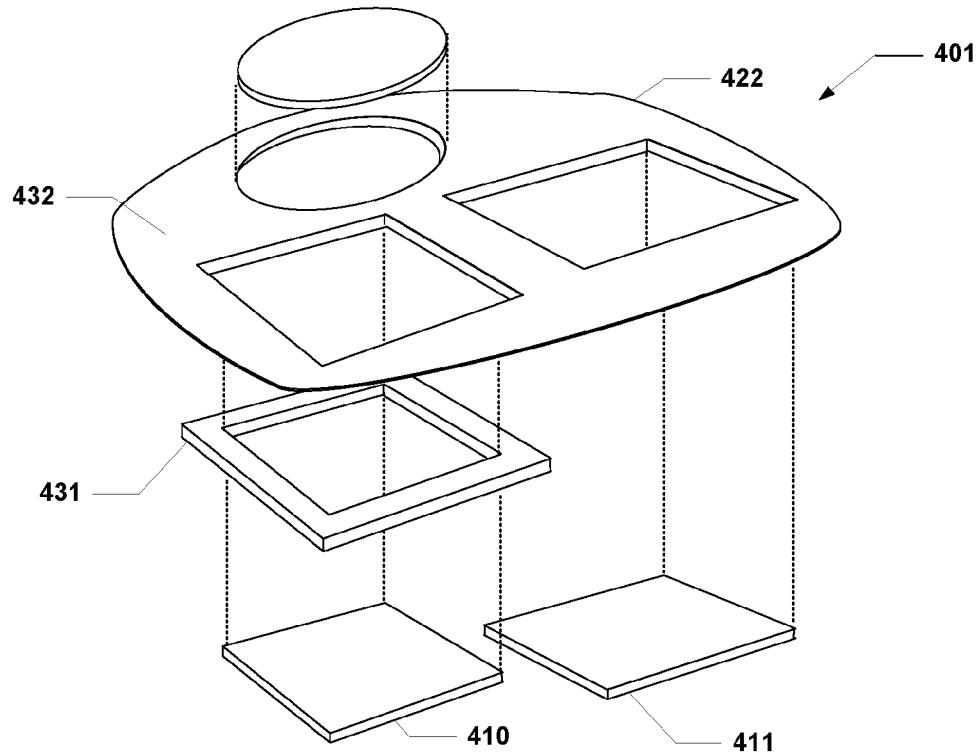
Figure 4C:
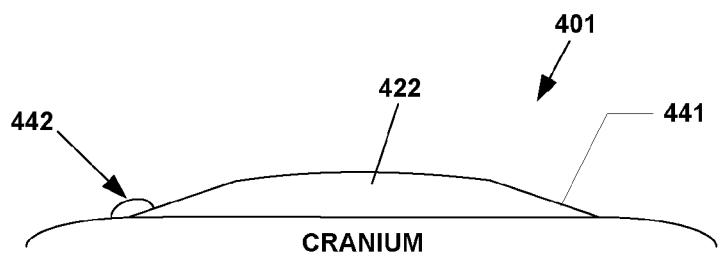

FIGS. 4A-4C are schematic diagrams illustrating a member 422 of a modular implantable medical device 401. FIG. 4A illustrates that the modular implantable medical device 401 comprises a set of modules 410-412, and a set of motion reduction elements 421 within member 422, such as motion reduction fibers connecting modules 410 and 411. Modules 410 and 411 are also coupled by a coupling module 423.

Because member 422 and coupling module 423 are flexible, member 422 and coupling module 423 may not provide sufficient motion reduction for the modules 410-412. Specifically, excessive relative motion between modules 410 and 411 may compromise the structural integrity of coupling module 424, which may lead to failure of modular implantable medical device 401. Motion reduction elements 421 are used to provide sufficient structural integrity to the device 401 once implanted into the patient 100 by restricting relative motion between modules 410 and 411 to certain directions or within certain ranges. Additional details regarding motion reduction elements 421 are described in co-pending and commonly assigned U.S. Pat. No. 7,392,089 to Wahlstrand et al., entitled "REDUCING RELATIVE INTERMODULE MOTION IN A MODULAR IMPLANTABLE MEDICAL DEVICE."

FIG. 4B illustrates that the member 422 may include two or more components, each component made of a different material. In particular, FIG. 4B illustrates the member 422 includes an elastomeric component 430 and a non-elastomeric component 431. The non-elastomeric component 431 is typically shaped to surround at least one of modules 410-412, i.e., is located proximate to sides of at least one of modules 410-412. In some embodiments, a plurality of individual non-elastomeric components 431 surround respective modules 410-412. In other embodiments, a non-elastomeric component 431 surrounds a plurality of modules 410-412 to integrate the surrounded modules in a common, semi-rigid structure.

The one or more non-elastomeric components 431 may be used to contain one or more modules within elastomeric component 430. Specifically, the one or more non-elastomeric components 431 may be formed to hold modules 410-412 within respective positions within elastomeric component 430. Elastomeric component 430 may, as shown in FIG. 4B, at least partially encapsulate each of modules 410-412 and provide an desired form factor for a modular implantable medical device. In some embodiments, non-elastomeric elements 431 are fitted into an elastomeric component 430 to form the member 422 before the electronic modules 410-412 are inserted into respective locations within member 422 where they will be contained by non-elastomeric elements 431.

Generally, member 422 provides a number of functions in including attaching to modules and other elements to provide a smooth interface surface for the device as it interacts with the patient, and protecting electrical connections and feed thru wires needed to connect modules to external leads.

Member 422 may be constructed from a durometric specific material to provide a clinically desirable device. In addition, a material used to construct the member 422 may possess a thermal conductivity characteristic to either act as a heat sink if needed to dissipate heat from modules 410-412, or a material to act as an insulator to shield the patient 100 from any excess heat from modules 410-412. Because the implantable medical device 401 may be constructed from a large number of modules to perform a desired task, the materials selected for used in constructing the member 422 may vary as needed by each embodiment.

In embodiments in which member 422 is constructed of components 431 and 432, the device 401 may be fabricated by integrating components 431 and 432 to form the member 422, constructing the modules 410-412 and their respective connection modules 423, and constructing any motion reduction elements 421. Once all of these components are fabricated, the motion restriction elements 421 may be combined with the member 422, and the interconnected modules 410-412 may be inserted into the member 422 into respective positions where they are contained by components 431.

FIG. 4C illustrates that the member 422 provides sloped interface 441 between the modules within the device 401 and the patient's body components. In embodiments in which the device 401 is implanted within tight spaces, such as under the scalp, the sloped interface 441 provides a smooth transition between the body and the device modules 410-412. Protrusions are known to cause possible stress points for tissue that is located over implanted devices, which can, for example, lead to skin erosion in the case of a device implanted under the scalp. As such, the sloped interface 441 attempts to minimize the transition from the modules 410-412 and the edge of the device 401 to eliminate these points of stress. An angle of interface 442 from the patient's body and the sloped interface 441 is greater than 90 degrees. Angle 442 may be between 120 and 150 degrees, is preferably between 130 and 140 degrees, and is most preferably approximately 135 degrees.

Figure 5A:
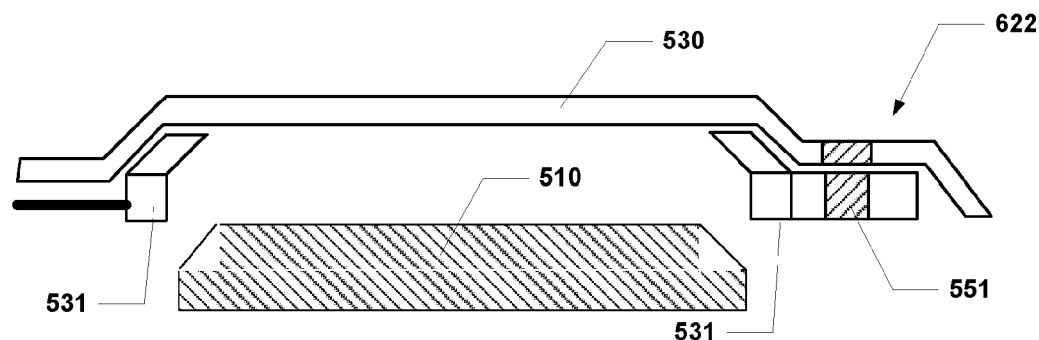
FIGS. 5A-5B are schematic diagrams illustrating the interaction of components of a member according to the present invention.
Figure 5B:
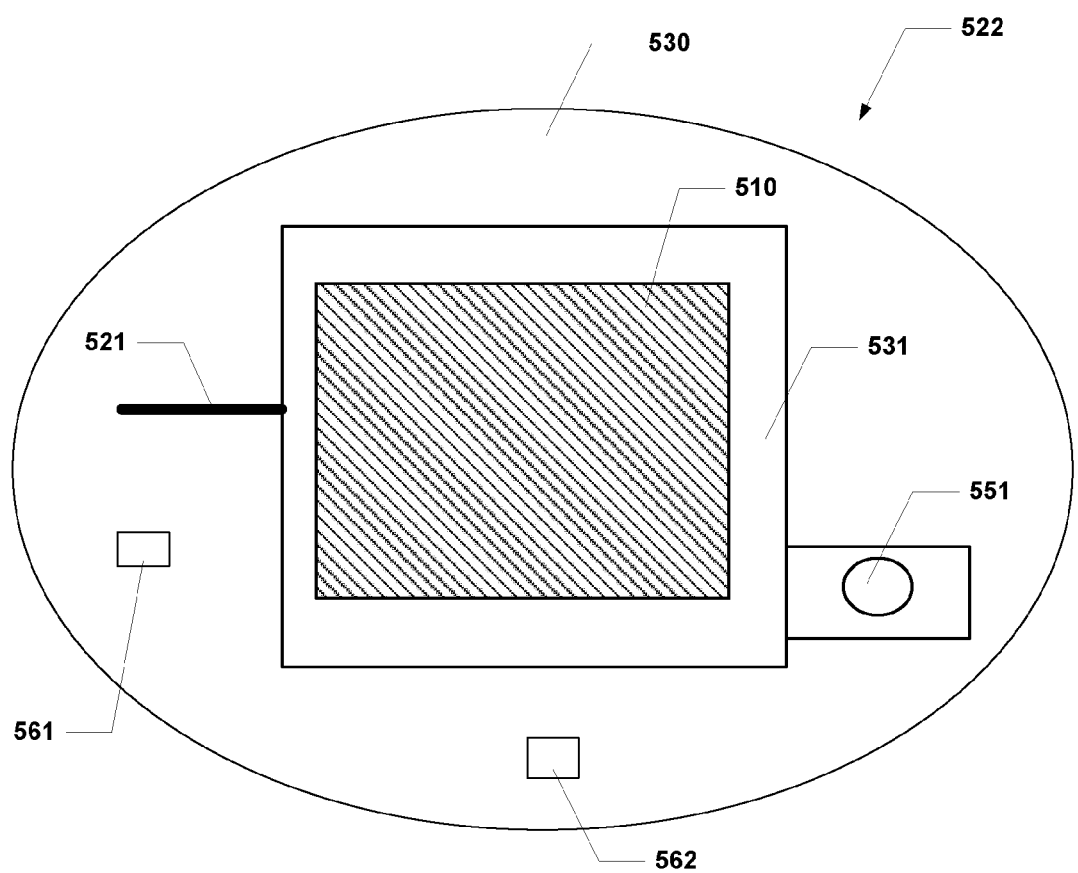

FIGS. 5A-5B are schematic diagrams illustrating the interaction of components of an implantable medical device that are part of a member. FIG. 5A provides a side cross-sectional view of a member 522 that includes an elastomeric component 530 and a non-elastomeric component 531 that interfaces with a control module 610. The non-elastomeric component 531 is shaped to mate with and surround the module 510, and may provide motion reduction for the module. Specifically, the non-elastomeric component 531 may be mechanically connected to at least one other module of a modular implantable medical device, e.g., to non-elastomeric components that surround other modules of an implantable medical device, by a motion reduction element 521. In other words, the member 522 encapsulates a plurality of modules in this embodiment, and each of the modules may be surrounded by a non-elastomeric component 531 that is connected to other non-elastomeric components by motion reduction elements 521.

A through hole 551 may be located through member 522, e.g., through elastomeric component 530 and non-elastomeric component 531, to provide an attachment point for the implantable medical device. In some embodiments, the implantable medical device may be secured in place using bone screws or similar attachment devices that secure the device to the patient. Such through holes 551 permit the device to be mechanically attached to the patient once the device is positioned at a desired location.

In addition, elastomeric component 530 is shown as completely encapsulating the modules and components within FIG. 5. However, in some embodiments, elastomeric component 530, like non-elastomeric component 531, may merely surround the module 510 but not cover the top of the module. Such an arrangement may render the profile of the overall device smaller. In such an alternate embodiment, a surface across the member and the electronics module 510 may minimize transition discontinuities to minimize profile changes that may interact with a patient after implantation. In other embodiments, one or both components 530 and 531 cover a top of module 510, or fully encapsulate module 510.

FIG. 5B illustrates a top view of the member 522 having an elastomeric component 530 that covers a non-elastomeric component 531 that surrounds the control module 510. The through hole 551 used as an attachment point is shown as part of the non-elastomeric component 531 that is covered by the elastomeric component 530. The shape of the non-elastomeric component 531 and control module 510 are shown as being rectangular in this embodiment. However, one skilled in the art will recognize that any shape for the non-elastomeric component 531 and control module 510 may be used without deviating from the spirit and scope of the present invention. Further, the shape of non-elastomeric component 531 need not be the same as that the shape of the component that it surrounds. The modules may be restrained within the member 522 using many restraint mechanisms known in the arts including attachment elements, adhesives, snap rings, and similar elements.

While the member 522 described above may be constructed from two different materials, a softer, more flexible elastomeric component 530 and one or more harder, more rigid non-elastomeric components 531, one skilled in the art may recognize that a member 522 may include a single component made of either class of material to provide the surface smoothing, module integration, and structural module restraint features described herein.

Finally, the member 522 may include several additional features unrelated to the above functions regarding the restraint and interconnection of multiple modules. In one embodiment, radio-opaque markers 561 and 562 may be imbedded within the member 522 to assist in determining an exact location of an implantable medical device within a patient. These radio-opaque markers 561 and 562 typically possess a non-symmetrical shape to permit registration and orientation of the device 501 from imaging of the markers. These radio-opaque markers may be constructed using barium and similar materials that permit such imaging. A telemetry and/or recharge coil may be embedded directly within the member 522.

It will be understood that an anti-infection agent and/or lubricious material may be disposed on or impregnated in at least a portion of an implantable medical device. A lubricious material is any material that when applied to an implantable medical device reduces the friction between the implantable medical device and the adjacent tissue. In one embodiment, the anti-infection agent and/or lubricious material may be disposed on or impregnated in the housing. For example, an anti-infection agent and/or lubricious material may be disposed on or impregnated in the housing 90 in FIG. 1A. In another embodiment, the anti-infection agent and/or lubricious material may be disposed on or impregnated in the member. For example, the anti-infection agent and/or lubricious material may be disposed on or impregnated in the member 94 in FIG. 1B. Disposing a lubricious material on or impregnated in a medical device may facilitate insertion of the device into the implantation location. The lubricious material may also reduce post-implant friction between a portion of the medical device and the adjacent tissue.

It may be desirable to apply the anti-infection agent and/or lubricious material to less than the entire outer surface of the device. In the case of an implant between the brain and scalp, the lubricious material may be disposed on the side of the device facing the scalp and therefore provide for easier insertion of the device under the scalp as well as reduce post implantation friction between the device and the scalp or other tissue. For example, in the case of device 90 when implanted between the brain and scalp, the convex side of the member 94 may be coated with a lubricious material 98 to reduce friction between the scalp and the device 90. The anti-infection agent may be applied to the concave side of the device.

Any known or future developed lubricious material, or combinations thereof, may be used. Preferably, the lubricious materials are medically suitable for inserting into a patient. Examples of suitable lubricous materials that may be disposed on at least a portion of a component of an implantable medical device include fluoroethylpolymer, polytetrafluoroethylene (PTFE), polyetheretherketone (PEEK), ethylene tetrafluoroethylene (ETFE), paralene, a hydrophilic polymer, and the like. Additional examples of suitable coating that may be applied include those described in the following patents and patent publications: US 20040030159; U.S. Pat. Nos. 6,558,734, 6,278,018; 6,603,040; 6,669,994; WO0121326; WO 0144174; and WO 2003055611. In an embodiment, the lubricious material is a hydrogel. The hydrogel may be a polyvinyl pyrrolidone (PVP) hydrogel, such as Medtronic's BIOGLIDE. In addition to facilitating insertion of a device, a lubricious material such as a hydrogel may prevent infection, thrombosis and formation of a fibrous capsule around the device. For example, BIOGLIDE technology has been shown to resist protein deposition, adherence of thrombosis, and reduce platelet and complement activation and may also inhibit tissue adherence.

Any known or future developed method for applying the anti-infection agent and/or lubricious material to either the housing or member may be utilized. In one embodiment, the lubricious material may be applied to the housing or member by being sprayed onto the surface of the housing or member. In another embodiment, the housing or member may be placed into the anti-infection agent and/or lubricious material allowing the anti-infection agent and/or lubricious material to be retained on or become impregnated in the housing or member.

Figure 15:
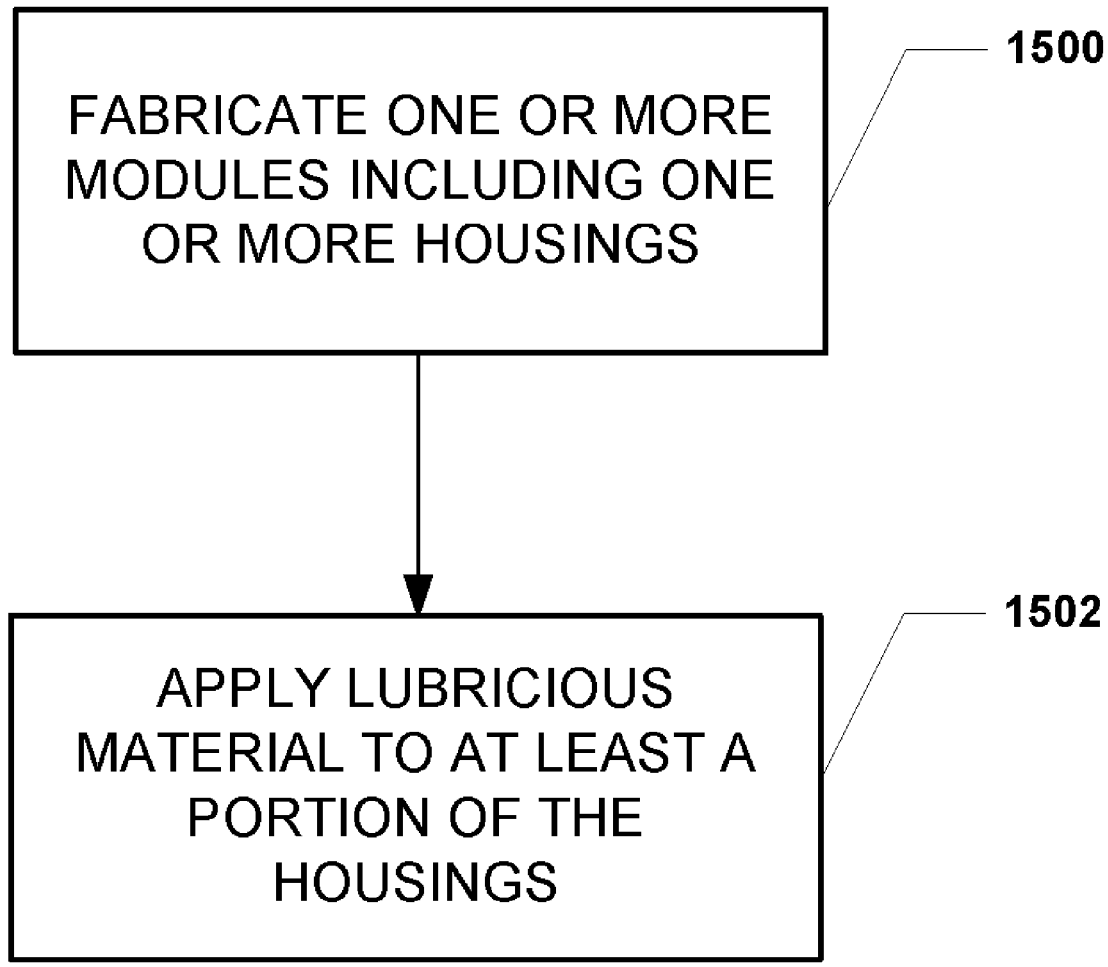
FIG. 15 is a flowchart illustrating a method of fabricating an implantable medical device including a lubricious material on or impregnated in the housing according to one embodiment of the present invention.

FIG. 15 is a flowchart illustrating one embodiment method of fabricating an implantable medical device including a lubricious material on the housing of the module. In this method, the module or modules of the device 80 are fabricated at step 1500. At step 1502 a lubricious material is applied to at least a portion of the housing 82 or multiple housings of the device 80. It should be understood that the lubricious material may be applied to the housing either prior to assembly of the components within the housing or after such assembly. Moreover, when multiple modules are used, the lubricious material may be applied to the housings before or after coupling the modules to each other.

Figure 16:
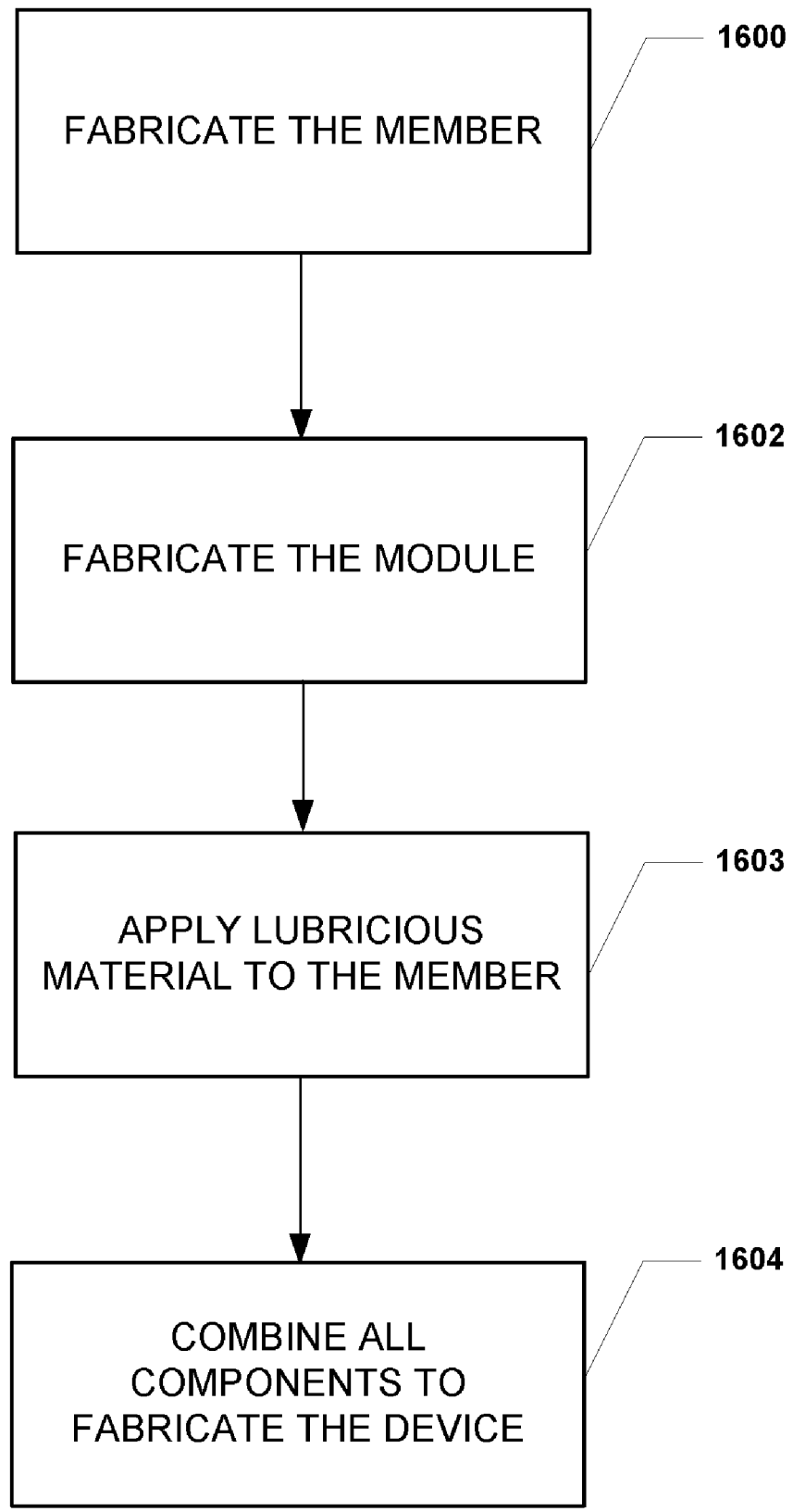
FIG. 16 is a flowchart illustrating a method of fabricating an implantable medical device including a lubricious material on a member according to one embodiment of the present invention.

FIG. 16 is a flowchart illustrating another embodiment method of fabricating an implantable medical device including a lubricious material on a member. In this method, the member is fabricated at step 1600. The fabrication of the member can be by any known or future developed method. At step 1602, a module is fabricated. At step 1604, a lubricious material is applied to the member. The components including the member and module are combined at step 1604. As described with regard to the process of FIG. 15, assembly and application of the lubricious material may be performed in any order.

Additional techniques for applying an anti-infection agent are available. As discussed above, the anti-infection agent may be impregnated into the housing or member or it may be applied on the housing or member as a coating. Alternatively, the anti-infection agent may be incorporated into (via compounding or other methods) into a thin jacket, pouch, sleeve or thin cover that fits at least partially around the housing. For example, coating layer 86 in FIG. 1A or coating layer 98 in FIG. 1B (or any other coating of any of the implantable medical device embodiments) may be an anti-infection coating. Such coatings may be anti-infection agent, lubricious material or a combination lubricious material and anti-infection agent.

Any antimicrobial agent, such as an antibacterial agent, an antiseptic agent, etc., may be used to prevent infection. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver sulfadiazine and alcohols. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include those listed above, as well as minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

An antimicrobial agent may be incorporated into or on the housing or member or a lubricious material using any known or future developed technique. For example, the antimicrobial agent may be disposed in or on the member or underlying coating layer (in one exemplary embodiment the underlying coating layer may be a lubricious material) through compounding or solvent expansion/swelling techniques. A hydrogel, for example, may be presoaked in a solvent comprising the anti-infection agent to incorporate the agent. Alternatively, an antimicrobial agent may be covalently attached to a housing or member or coating material using any known or future developed technology. Suitable technology includes Surmodic's PHOTOLINK technology. Conventional TDMAC (Tridodecylmethylammonium) coating technology, such as with TDMAC-heparin (Tridodecylmethylammonium heparinate), may also be employed. Additional technology for incorporating a therapeutic agent into or on a housing or member that may be used in accordance with the teachings of the present invention are discussed in, for example, U.S. Pat. Nos. 6,303,179, 6,143,354, 5,217,493, US 2004/0039437, and WO 04/014448. Of course any other therapeutic agent may be incorporated into or on the housing or member or lubricious coating.

As discussed above, another embodiment may utilize coating layers to apply the anti-infection agent to the housing or member. Depending upon the type of materials used to form coating layers, the coatings can be applied to the surface of the housing or member or an underlying coating layer through any coating processes known or developed in the art. One method includes directly bonding the coating material to a surface of the housing or member or underlying coating layer. By directly attaching a polymer coating to the housing or member or underlying coating layer, covalent chemical bonding techniques may be utilized. Housing or member or underlying coating layer surface may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, and etching with strong organic solvents. Alternatively, the coating layer may be indirectly bound to the member or housing or underlying coating layer through intermolecular attractions such as ionic or Van der Waals forces.

An anti-infection agent may also be incorporated into a coating layer in a variety of ways. For example, anti-infection agent may be covalently grafted to a polymer of the coating layer, either alone or with a surface graft polymer. Alternatively, an anti-infection agent may be coated onto the surface of the polymer or member either alone or intermixed with an overcoating polymer. An anti-infection agent may be physically blended with a polymer of a coating layer as in a solid-solid solution. Anti-infection agent may be impregnated into a polymer by swelling the polymer or member in a solution of the appropriate solvent. Any means of incorporating anti-infection agent into or on a coating layer may be used, provided that anti-infection agent may be released, leached or diffuse from coating layer, member or housing on contact with bodily fluid or tissue.

A polymer of a coating layer and an anti-infection agent may be intimately mixed either by blending or using a solvent in which they are both soluble. This mixture can then be formed into the desired shape or coated onto an underlying structure of the medical device. One exemplary method includes adding one or more anti-infection agents to a solvated polymer to form a anti-infection agent/polymer solution. The anti-infection agent/polymer solution can then be applied directly to the surface of a member (such as member 94 for example) or housing (such as housing 82), or an underlying coating layer (such as coating layer 98 or 86 for example); by either spraying or dip coating the housing or member. As the solvent dries or evaporates, the anti-infection agent/polymer coating is deposited on the member or housing. Furthermore, multiple applications can be used to ensure that the coating is generally uniform and a sufficient amount of anti-infection agent has been applied.

Alternatively, an overcoating polymer, which may or may not be the same polymer that forms the primary polymer of the member or underling coating layer 25, and anti-infection agent are intimately mixed, either by blending or using a solvent in which they are both soluble, and coated onto member or housing or underling coating layer. Any overcoating polymer may be used, as long as the polymer is able to bond (either chemically or physically) to the member or housing.

In addition, a polymer of a coating layer may be swelled with an appropriate solvent, allowing a anti-infection agent o impregnate the polymer.

Anti-infection agent may also be covalently grafted onto a polymer of a coating layer. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), may be used to initiate surface grafting.

Figure 17:
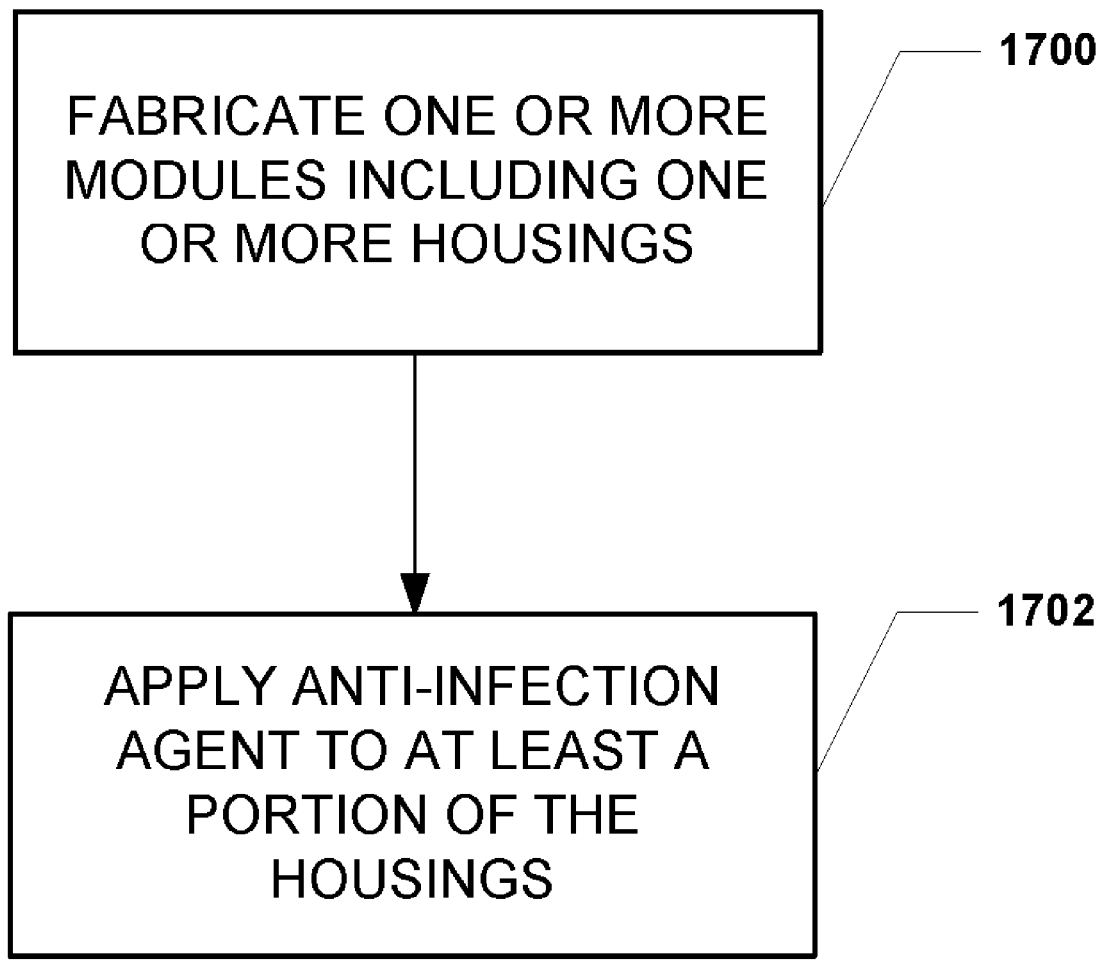
FIG. 17 is a flowchart illustrating a method of fabricating an implantable medical device including an anti-infection agent on or impregnated in the housing according to one embodiment of the present invention.

FIG. 17 is a flowchart illustrating one embodiment method of fabricating an implantable medical device including an anti-infection agent on the housing of the module. In this method, the module or one or more modules of the device 80 are fabricated at step 1700. At step 1702 an anti-infection agent is applied to at least a portion of the housing 82 or multiple housings of the device 80. It should be understood that the anti-infection agent may be applied to the housing either prior to assembly of the components within the housing or after such assembly. Moreover, when multiple modules are used, the anti-infection agent may be applied to the housings before or after coupling the modules to each other.

Figure 18:
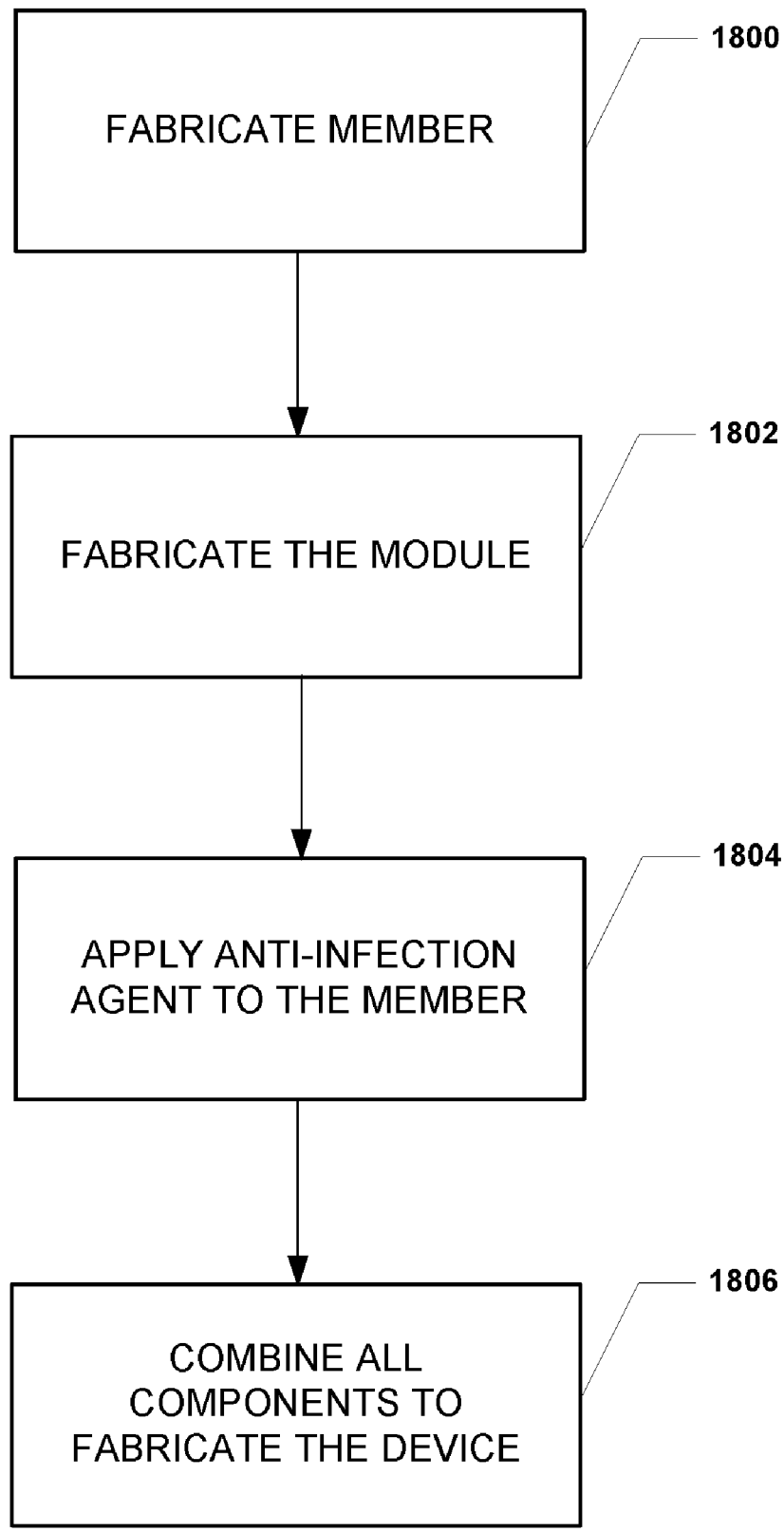
FIG. 18 is a flowchart illustrating a method of fabricating an implantable medical device including an anti-infection agent on or impregnated in a member according to one embodiment of the present invention.

FIG. 18 is a flowchart illustrating another embodiment method of fabricating an implantable medical device including an anti-infection agent on a member. In this method, the member is fabricated at step 1800. The fabrication of the member can be by any known or future developed method. At step 1802, a module is fabricated. At step 1804, an anti-infection agent is applied to the member. The components including the member and module are combined at step 1806. As described with regard to the process of FIG. 17, assembly and application of the anti-infection agent may be performed in any order.

Figure 6:
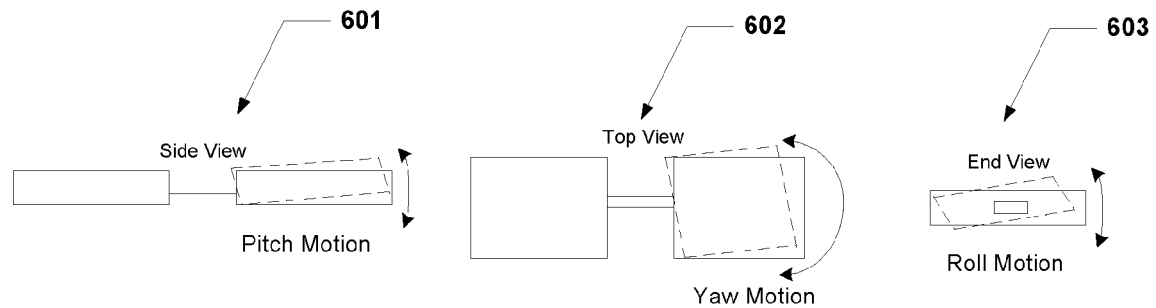
FIG. 6 is a schematic diagram illustrating the degrees of motion present in a modular implantable medical device.

FIG. 6 is a schematic diagram illustrating degrees of inter-modular motion that may be present in modular implantable medical device. For any two modules within a distributed medical device, motion between the two modules may include pitch motion 601, yaw motion 602, and roll motion 603. For the set of motion reduction elements 621 discussed above, one or more of these three degrees of motion may be limited to prevent mechanical failures of interconnections between the modules during use of a modular implantable medical device. Specifically, modules of a modular implantable medical device may be connected by connector modules, which may be compromised by excessive intermodule motion. Such interconnect members are described in greater detail in commonly assigned U.S. Pat. No. 7,392,089 to Wahlstrand et al., entitled "REDUCING RELATIVE INTERMODULE MOTION IN A MODULAR IMPLANTABLE MEDICAL DEVICE."

Figure 7:
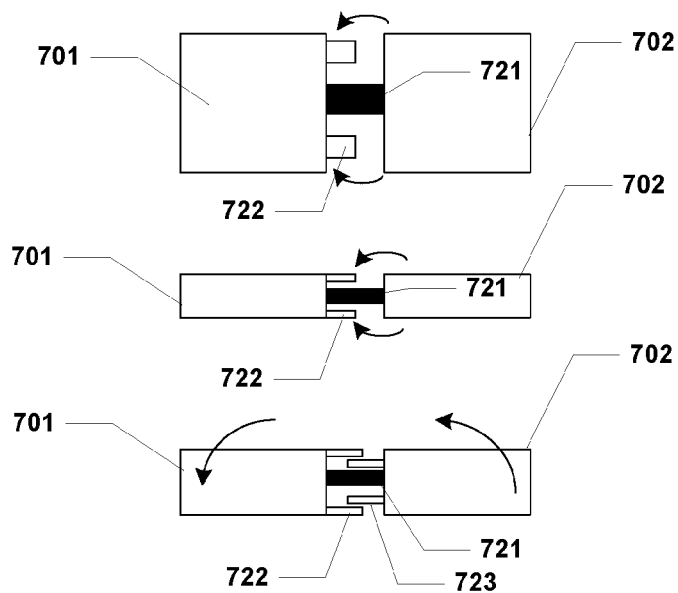
FIG. 7 is a schematic diagram illustrating motion reduction within various degrees of motion within a modular implantable medical device.

FIG. 7 is a schematic diagram illustrating motion reduction within various degrees of motion within a modular implantable medical device. For any two modules 701-702 within an implantable medical device, a connector module 721 may be used between the modules 701-702 to connect elements within these modules 701-702. Motion reduction elements 722 and 723 may be used to reduce inter-modular motion, and in some cases, to limit inter-modular motion to a range of motion.

Motion reduction elements 722 and 723 may be formed as part of non-elastomeric components 531 of a member 522 associated with each of modules 701 and 702. As shown in FIG. 7, motion reduction elements 722 and 723 allow free inter-modular motion within one of the degrees within a range. In some embodiments, one non-elastomeric component includes one or more motion reduction elements 722. In other embodiments, two non-elastomeric components 531 include motion reduction elements 722 and 723, respectively, which interact to reduce inter-modular motion.

A modular implantable medical device may include any number of motion reduction elements, which may take any of a variety of shapes. In some embodiments, motion reduction elements may be used in all axes to maximize the amount of motion reduction provided. The implantable medical device having multiple modules typically requires sufficient motion reduction to prevent undue mechanical stresses on interconnection connection member 721 between the modules 701-702 that may not be provided by a flexible member 522.

Additional details regarding the set of motion reduction elements 521 are described in co-pending and commonly assigned U.S. Pat. No. 7,392,089 to Wahlstrand et al., entitled "REDUCING RELATIVE INTERMODULE MOTION IN A MODULAR IMPLANTABLE MEDICAL DEVICE."

Figure 8A:
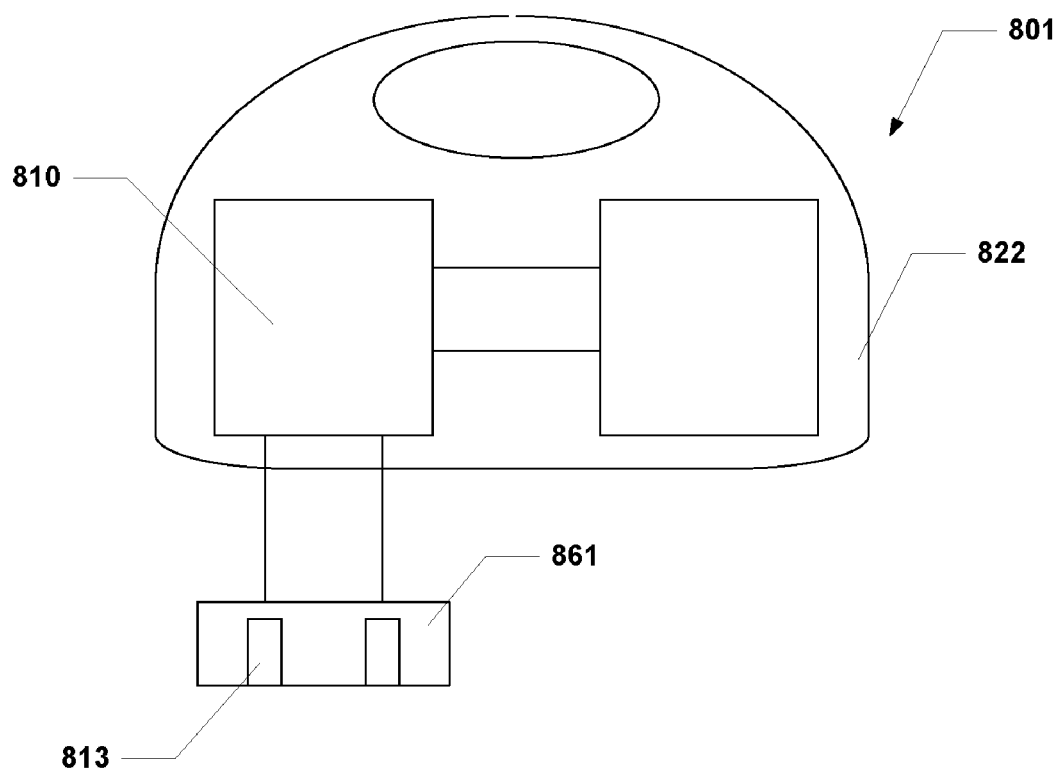
FIGS. 8A-8C are schematic diagrams illustrating example embodiments of modular implantable medical devices having lead management features.

FIG. 8A is a block diagram illustrating an example embodiment of a modular implantable medical device 801 having a tethered lead interconnect site 861 according to the present invention. A member 822 of implantable medical device 801 at least partially encapsulates and connects a plurality of modules 810-812 while not encapsulating lead connection modules 813 that are part of tethered lead interconnect site 861. In such embodiments, the implantation of device 801 would not require the insertion of external leads into the member 822. In addition, the external leads may be located a distance away from the device 801. Such an arrangement may assist in the management of the external leads as they are placed within the patient and routed to a device implantation location. Further, location of leads and connection site 861 away from member 822 may make it less likely that the leads will be damaged during a surgical explant procedure.

Figure 8B:
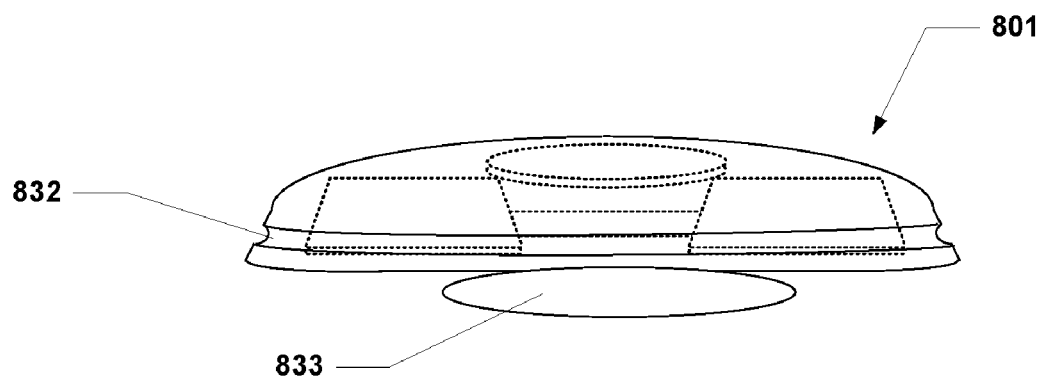
Figure 8C:
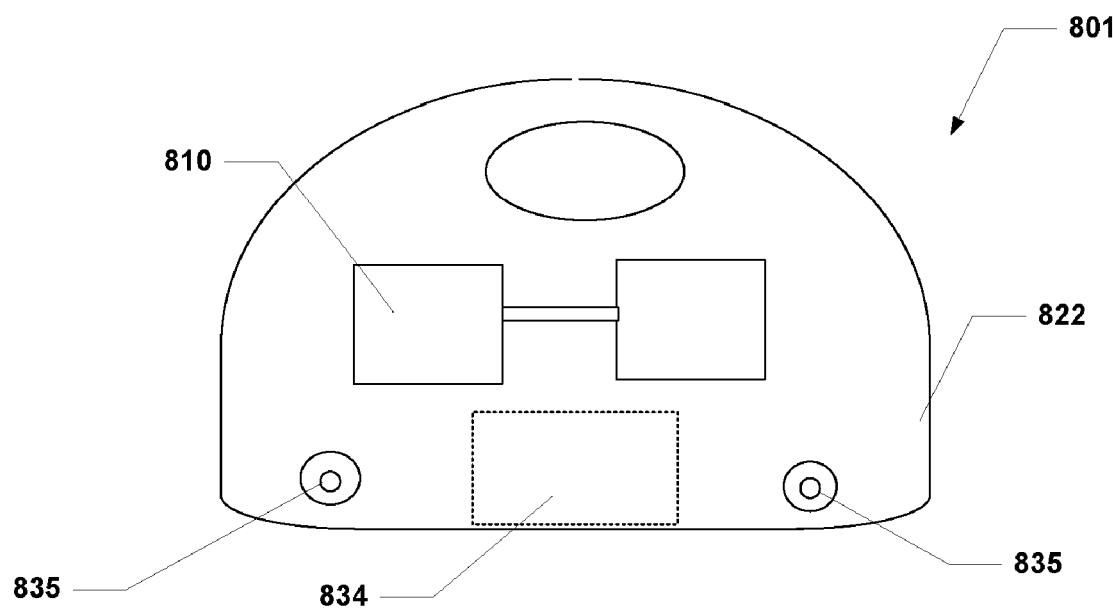

In alternate embodiments shown in FIGS. 8B-8C, member 822 may possess mechanical structures such as grooves 832, an externally attached pouch 833, or an integrated containment cavity 834 to contain and/or route the external leads away from the implantable medical device 801 in an efficient manner. In some embodiments, the external leads may possess a minimum length to provide a particular electrical characteristic for the implantable medical device 801. This minimum length may be greater than a distance needed by a particular patient for some implantation locations. These mechanical structures that assist in external lead management may accommodate any extra lead material that needs to be part of the device 801 in some implantation embodiments. Because the member may be spread over an area surrounding the modular device, the member may cover holes in the cranium formed to allow external leads to access the brain. Additional structures, including one or more cap structures 835 that secure a lead as it passes through the hole in the cranium may be an integral part of the member connector module 822.

Additional details regarding the lead connection modules are described in co-pending and commonly assigned U.S. Patent Application Publication No. 2004/0176816 by Singhal et al., entitled "LEAD CONNECTION MODULE OF A MODULAR IMPLANTABLE MEDICAL DEVICE."

Figure 9:
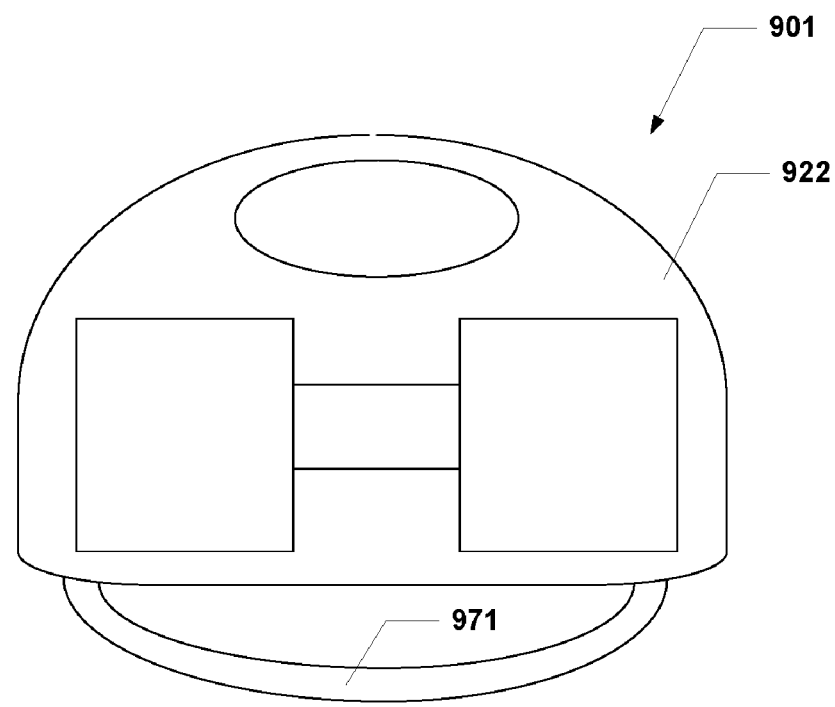
FIG. 9 is a schematic diagram illustrating an example embodiment of a modular implantable medical device having an access loop for removal.

FIG. 9 is a block diagram illustrating an example embodiment of a modular implantable medical device 901 having an access loop 971 for removal according to the present invention. Access loop 971 may be mechanically coupled to, or formed as a part of member connector module 922. This access loop 971 may be used to assist in the removal of the implantable medical device 901 at a point in time when the device 901 is no longer needed by the patient, or at a point in time when a particular device 901 needs to be replaced. The device 901 may be encapsulated within the patient 100 with scar tissue fibers such that physical effort will be required to remove the device 901 from its implantation location. This access loop 971 provides a clinician a removal assist structure to physically manipulate the implantable medical device 901 during its removal. This access loop 971 may also be useful during implantation of the device 901 as well as it provides a handle to manipulate the device 901 without handing the member 922 and its related modules. One skilled in the art will recognize that alternate embodiments for the access loop that may include removal handles, a strip cord and a reinforced opening within the member connector module to provide a mechanism to grasp the device to assist in removal.

Figure 10:
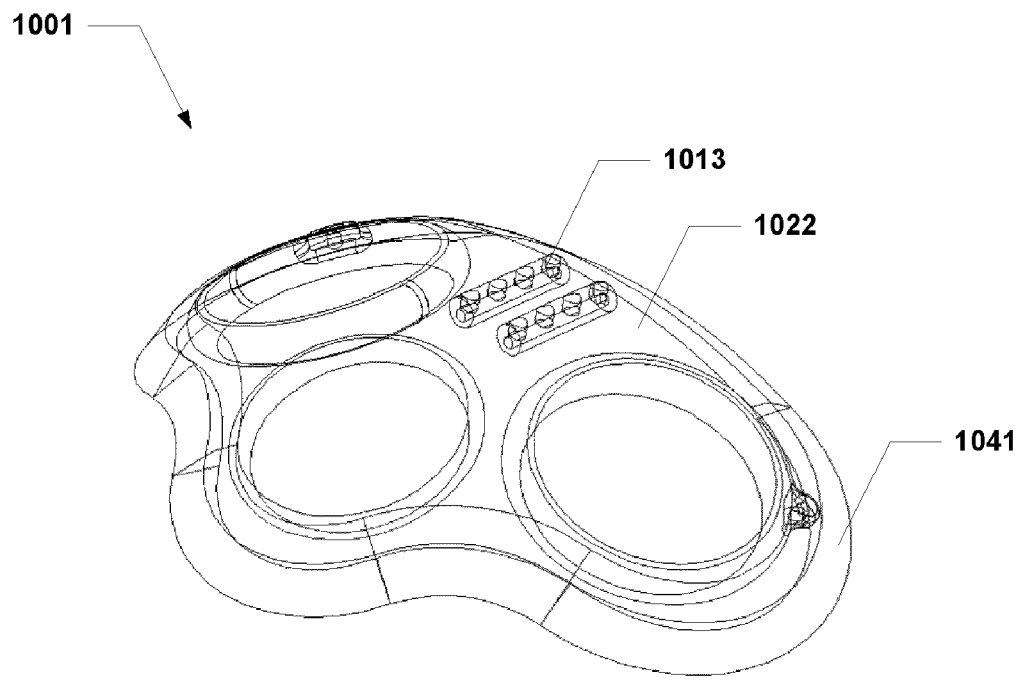
FIG. 10 is a schematic diagram illustrating a perspective view of an example embodiment of a modular implantable medical device having a triangular module arrangement.

FIG. 10 is a schematic diagram illustrating an example embodiment of a modular implantable medical device 1001 having a triangular module arrangement according to the present invention. In this embodiment, a triangular arrangement of modules is shown with a member 1022 that at least partially encapsulates all of the modules. Lead interconnection modules 1013 are located between the modules at a common location. Member 1022 provides a slope interface 1041.

Figure 11:
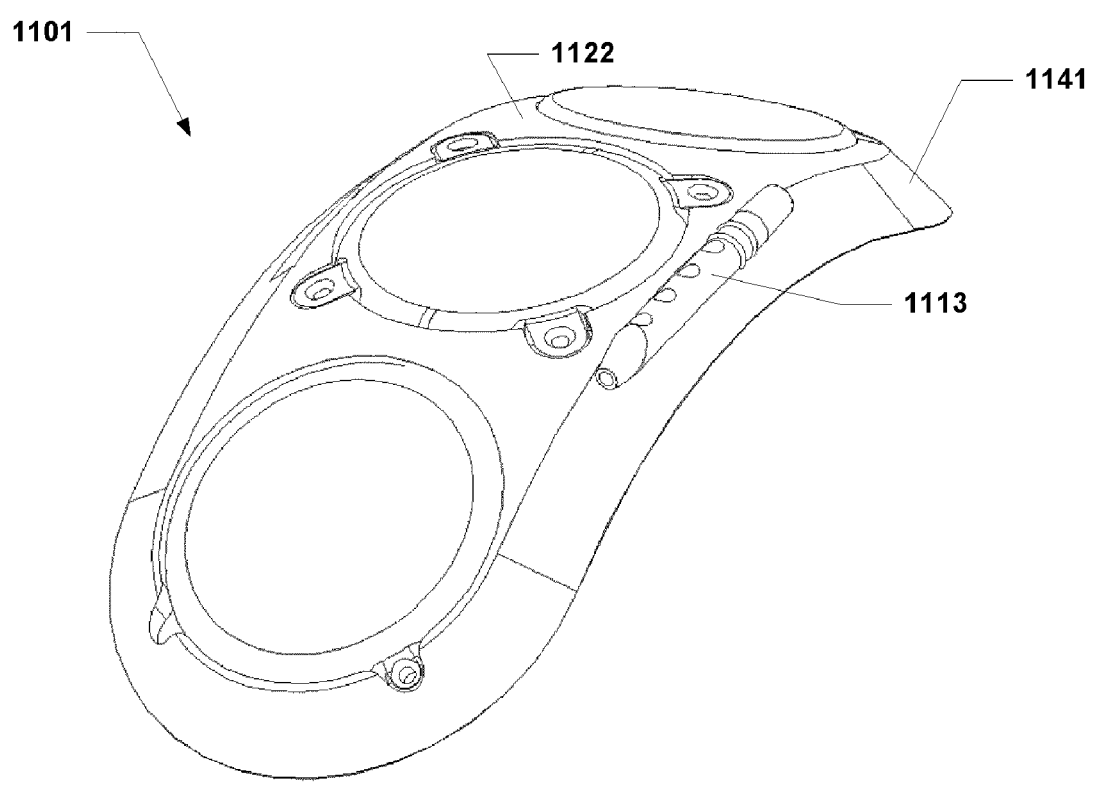
FIG. 11 is a schematic diagram illustrating a perspective view of an example embodiment of a modular implantable medical device having an inline module arrangement.

FIG. 11 is a schematic diagram illustrating an example embodiment of a modular implantable medical device 1101 having an inline module arrangement according to the present invention. In this embodiment, an inline arrangement of modules is shown with a member 1122 that at least partially encapsulates all of the modules. A lead interconnection module 1113 is located on one side of the member 1122. Member 1122 provides a slope interface 1141.

Figure 12:
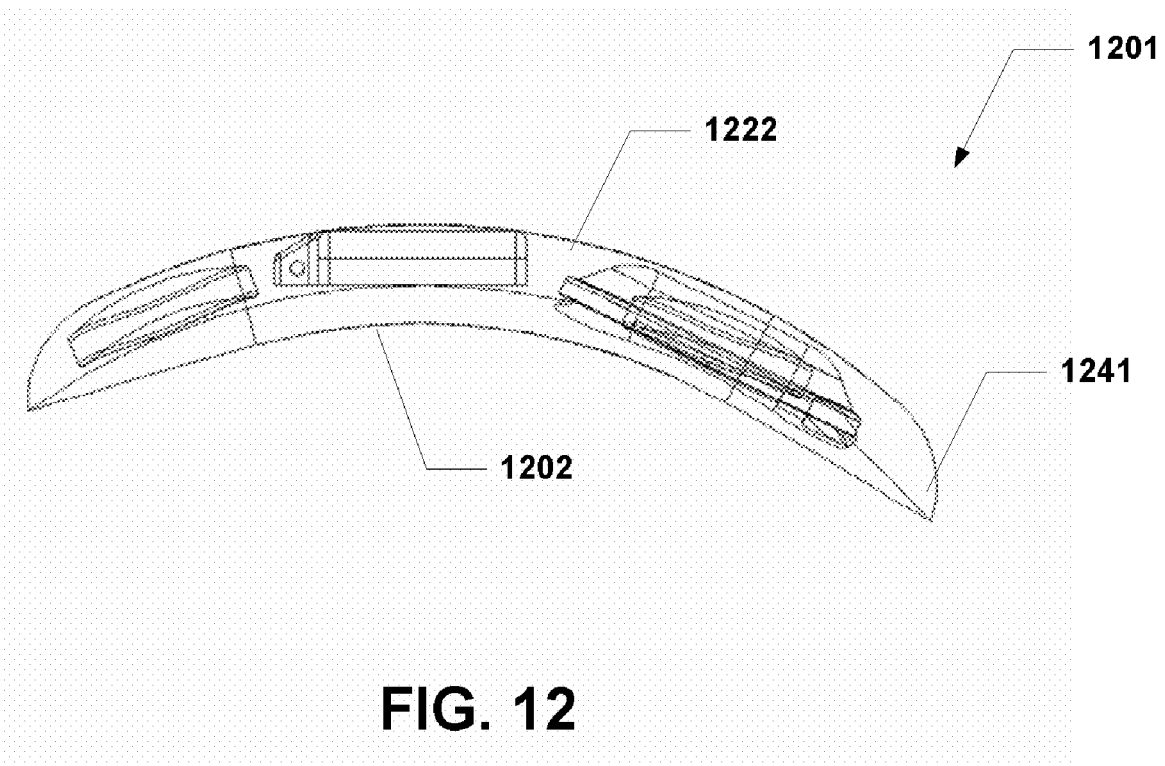
FIG. 12 is a schematic diagram illustrating side view of a modular implantable medical device having an inline module arrangement.

FIG. 12 is a schematic diagram illustrating side view of a multi-module implantable medical device having an inline module arrangement according to the present invention. The side view of the device 1201 shows an underside of the device 1202 that possess a curved shape to permit implantation at a location having a curved body structure.

Figure 13:
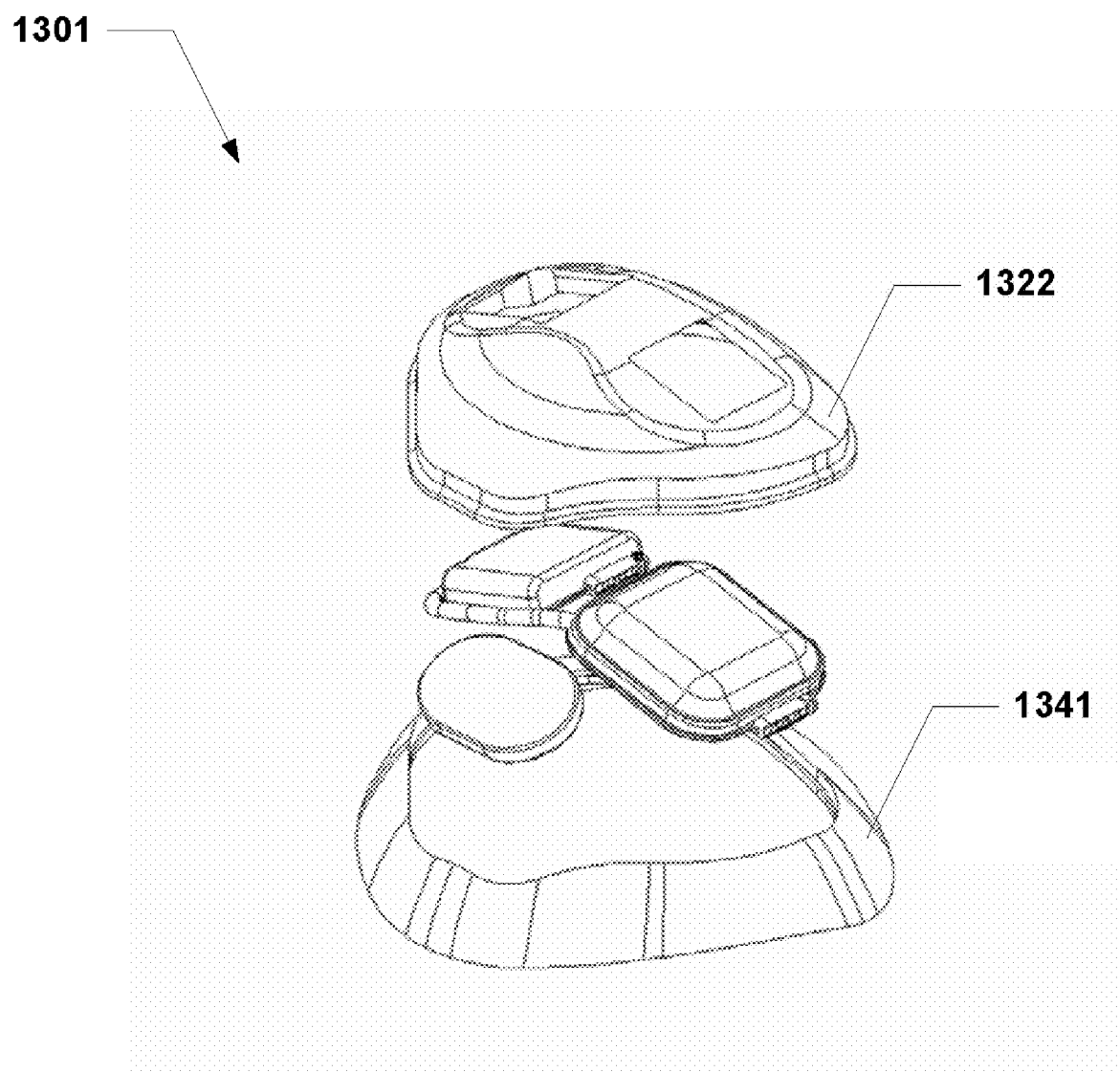
FIG. 13 is a schematic diagram illustrating an exploded view of a modular implantable medical device having a triangular module arrangement.

FIG. 13 is a schematic diagram illustrating an exploded view of a modular implantable medical device 1301 having a triangular module arrangement according to the present invention. In this embodiment, yet another triangular arrangement of modules is shown with a member 1322 at least partially encapsulating all of the modules. A slope interface element 1341 is shown surrounding the member 1322. In this embodiment, the slope interface element 1341 is shown as a separate physical structure, such as a flexible band, an o-ring, removable flexible flange, or a tapered outer contour element that surrounds the member 1322, rather than a tapered portion of member 1322. Slope interface element 1341 provides a desired sloped interface between the edge of the implantable medical device and the patient. In some embodiments, the shape and contour of slope interface element 1341 may be modified at the time of implantation to obtain a desired shape, or slope interface elements 1341 may be selected at the time of implantation from a variety of slope interface elements to provide a desired slope interface for a particular patient.

Figure 14:
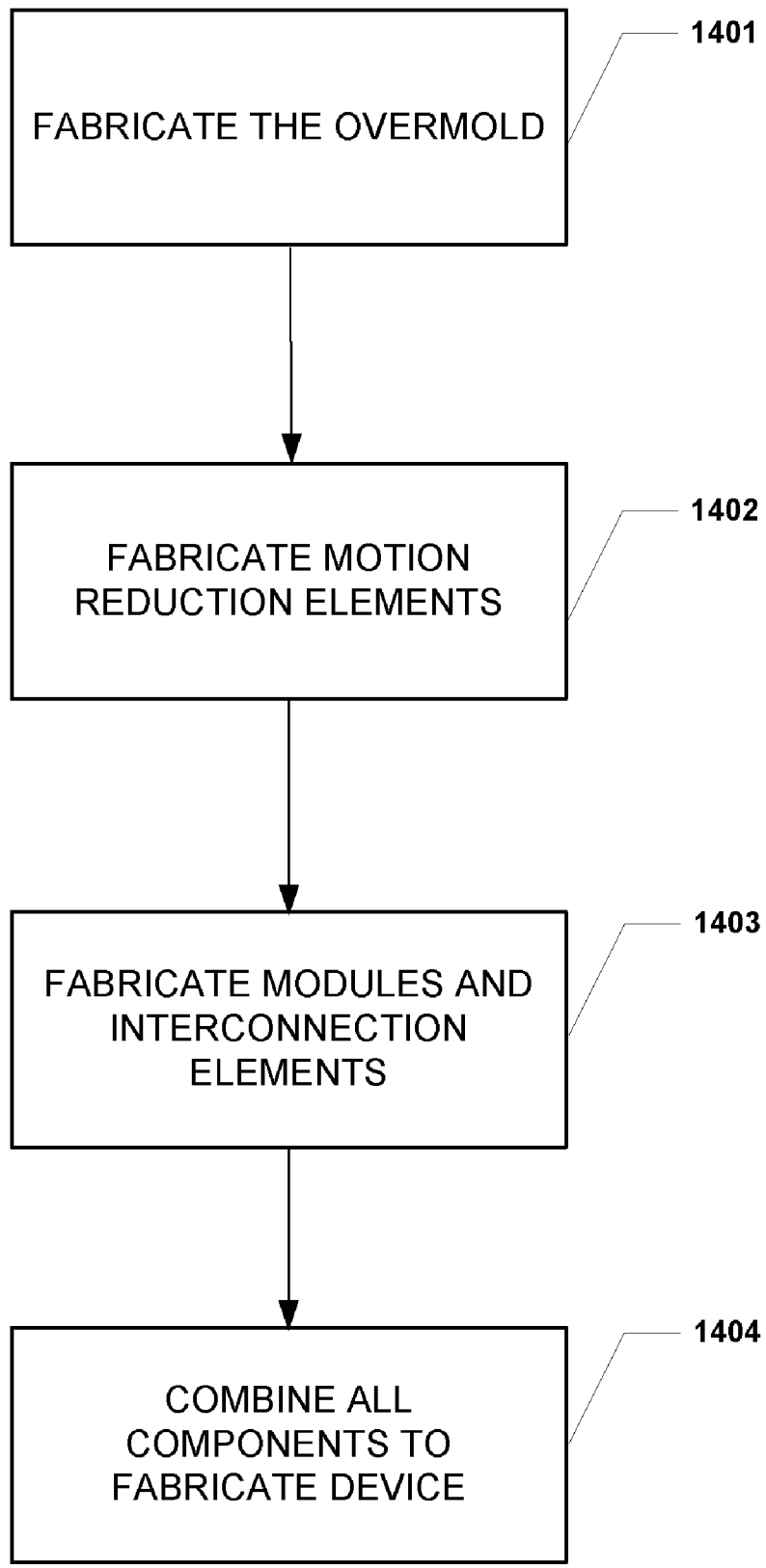
FIG. 14 is a flowchart illustrating a method of constructing an implantable medical device with a member according to the present invention.

FIG. 14 is a flowchart illustrating a method of constructing an implantable medical device with a member according to the present invention. An implantable medical device 401 may be fabricated by constructing the member 422 (1401) from a first and second component. As discussed above, member 422 may comprise two or more materials, and two or more components. For example, member may comprise one or more elastomeric components formed of an elastomeric material, such as silicone, and one or more non-elastomeric components formed of a non-elastomeric material. Once the member 422 is completed, the modules 410-412 with their respective connector modules 423 are constructed (1402). Next, any motion reduction elements 421 included in the device 401 are constructed. Once all of these components are fabricated, the motion restriction elements 421 may be combined with the member 422 (1403) and the interconnected modules 410-412 may be inserted (1404) into the member 422. From the combination of these components, the device 401 is formed.

It should be noted that the anti-infection agent and/or lubricious material may be on or impregnated in any of the embodiments of implantable medical devices provided even though such is not specifically called out in every Figure and accompanying description.

Figure 19A:
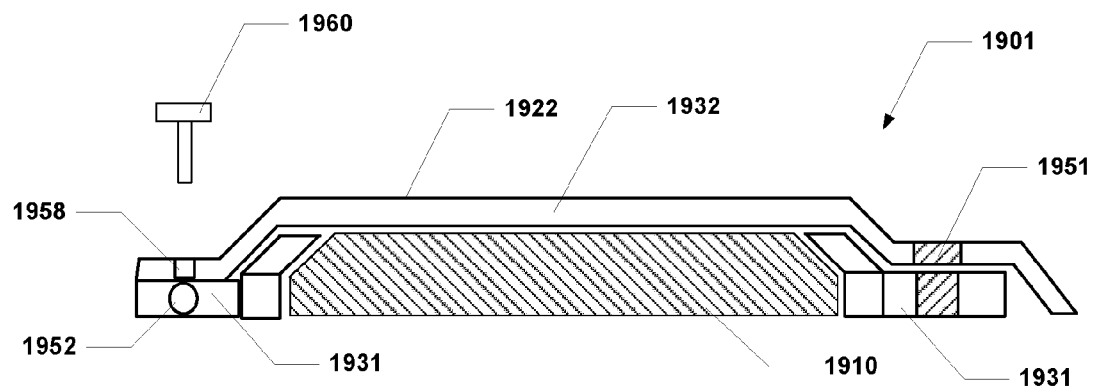
FIGS. 19A-19B are schematic diagrams illustrating another embodiment of an implantable medical device.
Figure 19B:
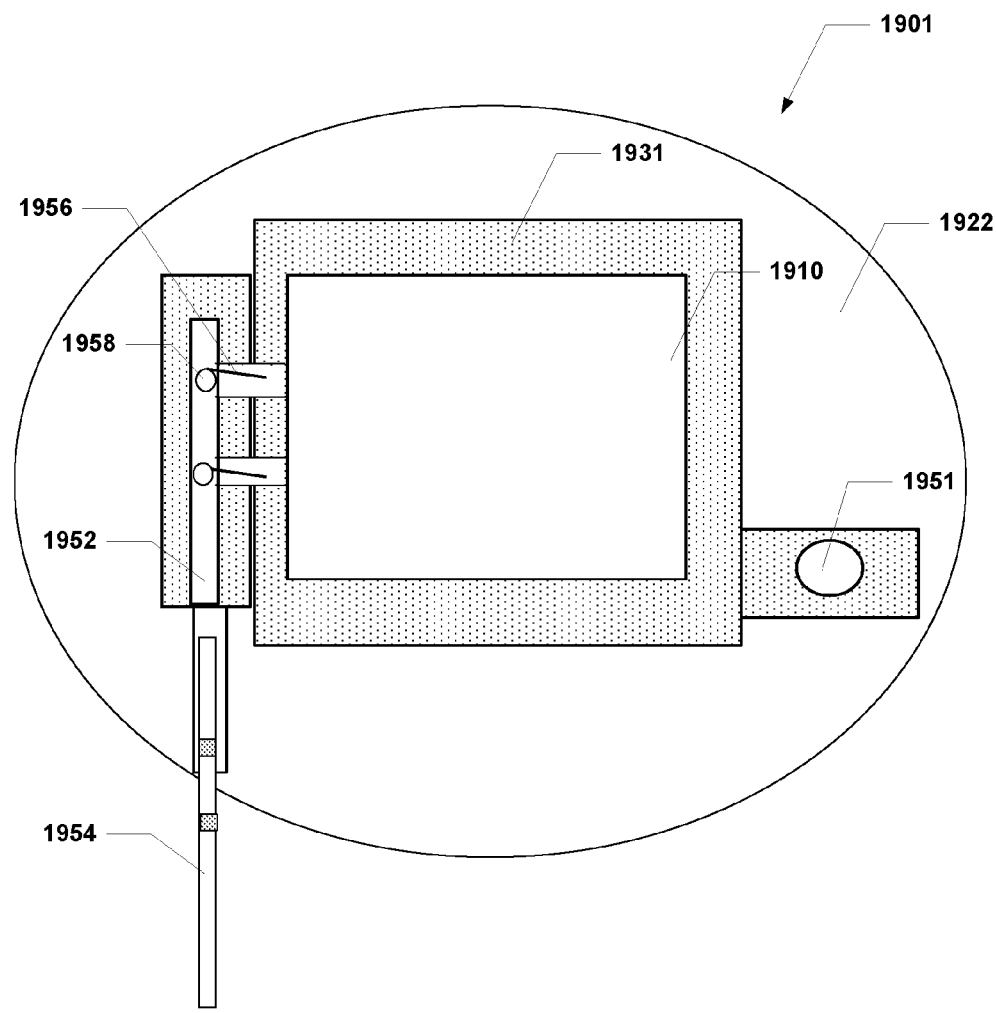

FIGS. 19A-19B are schematic diagrams illustrating an exemplary interaction of components of an IMD 1901. FIG. 19A provides a side view of an member 1922, which includes one or more soft or elastomeric components 1932 and one or more hard or non-elastomeric components 1931, which interface with a control module 1910. Non-elastomeric component 1931 may be shaped to mate with the module 1910 to provide motion restriction for the module. Non-elastomeric component 1931 may be mechanically connected to other modules using a motion restriction device (not shown). The member 1922 covers all of these components in this embodiment. A through hole 1951 may be located through the non-elastomeric component 1931 and elastomeric component 1932 to provide an attachment point for IMD 1901. In some embodiments, IMD 1901 may be anchored in place using bone screws or other anchoring devices. Through holes 1951 permit IMD 1901 to be mechanically anchored to the patient once the device 1901 is positioned at a desired location. In the embodiment shown in FIG. 19A, a bone screw inserted into through hole 1951 would seat against non-elastomeric component 1931, but the invention encompasses embodiments in which a bone screw would seat against another component, such as control module 1910.

FIG. 19B illustrates a top view of the device 1901 having elastomeric component 1932 of member 1922 covering the non-elastomeric components 1931 that frame control module 1910. The through hole 1951 used as an attachment point is shown as part of non-elastomeric component 1931 that is covered by elastomeric component 1932. The shape of non-elastomeric component 1931 and control module 1910 are shown as being rectangular in this embodiment. However, one skilled in the art will recognize that any shape for the non-elastomeric component 1931 and control module 1910 may be used without deviating from the spirit and scope of the present invention.

In both FIGS. 19A and 19B, a lead interconnect device 1952 is included within the non-elastomeric components 1931 of member 1922. In these examples, the non-elastomeric component 1931 restrains control module 1910 and external leads 1954, which are separate from lead interconnect device 1952. Typically, the external leads 1952 have iso-diametric proximal ends for connection of the external leads 1954 to IMD 1901. An external lead 1954 is inserted into the lead connection module in order to connect the external leads 1954 to electronics within control module 1910 of IMD 1901. This electrical connection from the control module 1910 to the external leads 1954 is made using a module connection lead wire 1956 that extends from control module 1910 and physically connects with the external lead 1954 within the lead connection module 1952.

The lead connection module 1952 may also include a mechanical lead securing mechanism 1958 that engages the external lead 1954 to restrain its motion and ensure electrical connection with feed-through wires 1956. In the embodiment of FIG. 19A, a tool 1960 is used to engage the mechanical lead securing mechanism 1958 within the lead connection module 1952. In this embodiment, the mechanical lead securing mechanism 1958 comprises a mechanical set-screw that is tightened by a screwdriver. An example of such a mechanical lead securing mechanism 1958 is a low-profile DBS lead extensions manufactured by Medtronic Inc. In alternate embodiments, the mechanical lead securing mechanism 1958 may be tool-less using a variety of known securing technologies that ensures the external lead 1954 does not separate from the lead connection module 1952. Tool-assisted or toolless coupling of leads to the IMD both allow medical personnel to couple leads to the IMD quickly and securely.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

The invention claimed is:

1. An implantable medical device comprising:
a module comprising a housing that contains at least a portion of electronics for providing monitoring of or therapy to a brain of a patient;
an anti-infection agent coated on or impregnated in at least a first portion of the housing; and
a lubricious material coated on or impregnated in at least a second portion of the housing, wherein the first and second portions of the housing are different sides, and wherein at least one of the anti-infection agent or the lubricious material is only coated on or impregnated in one side of the housing.

2. The implantable medical device of claim 1, wherein the module comprises a first module and the housing comprises a first housing, wherein the medical device further comprising a second module comprising a second housing, wherein the first and second modules are connected, and wherein the anti-infection agent is coated on or impregnated in the second housing.

3. The implantable medical device of claim 1, wherein the anti-infection agent is only coated on or impregnated in one side of the housing.

4. The implantable medical device of claim 1, wherein the housing comprises ceramic.

5. The implantable medical device of claim 1, wherein the housing defines a substantially concave side that includes the first portion of the housing.

6. The implantable medical device of claim 5, wherein the housing defines a substantially convex surface that includes the second portion of the housing.

7. The implantable medical device of claim 1, wherein the lubricious material comprises a polymer layer and wherein the anti-infection agent is impregnated in the polymer layer and the polymer layer is attached to the at least the second portion of the housing.

8. The implantable medical device of claim 1, wherein the lubricious material is electrically conductive.

9. An implantable medical device comprising:
a module comprising a housing that contains at least a portion of electronics for providing monitoring of or therapy to a patient;
a member at least partially encapsulating the module, wherein the member provides a smooth interface between at least a portion of the housing and tissue of a patient;
an anti-infection agent coated on or impregnated in a first portion of the member; and
a lubricious material coated on or impregnated in at least a second portion of the member, wherein the first and second portions of the member are different sides, and wherein at least one of the anti-infection agent or the lubricious material is only coated on or impregnated in one side of the housing.

10. The implantable medical device of claim 9, wherein the anti-infection agent is only coated on or impregnated in one side of the member.

11. The implantable medical device of claim 10, wherein the member defines a substantially concave side comprising the first portion of the member.

12. The implantable medical device of claim 11, wherein the anti-infection agent is only coated on or impregnated in the substantially concave side of the member.

13. The implantable medical device of claim 10, wherein the member defines a substantially convex side comprising the second portion of the member.

14. The implantable medical device of claim 13, wherein the lubricious material is only on the substantially convex side of the member.

15. The implantable medical device of claim 9, wherein the member is flexible.

16. The implantable medical device of claim 9, further comprising a lead connection module within the member for connecting an external lead to electronics within the module, wherein the external lead is separable from the lead connection module.

17. The implantable medical device of claim 9, wherein an edge of the member provides a sloped interface with a surface of the patient, and an angle between the edge and the surface of the patient is greater than 90 degrees.

18. The implantable medical device of claim 9, wherein the lubricious material is electrically conductive.

19. An implantable medical device comprising:
a module comprising a housing, wherein the housing contains at least a portion of electronics for providing monitoring of or therapy to a patient;
anti-infection means coated on or impregnated in at least a first portion of the housing; and
lubricious means coated on or impregnated in at least a second portion of the housing, wherein the first and second portions of the housing are different sides, and wherein at least one of the anti-infection means or the lubricious means is only coated on or impregnated in one side of the housing.

20. The implantable medical device of claim 19, wherein the anti-infection agent is absent from at least one side of the housing.

21. An implantable medical device comprising:
a module comprising a housing, wherein the housing contains at least a portion of electronics for providing monitoring of or therapy to a patient;
means for at least partially encapsulating the module, wherein the means for at least partially encapsulating the module provides a smooth interface between at least a portion of the housing and tissue of a patient;
anti-infection means coated on or impregnated in at least a first portion of the means for at least partially encapsulating the module; and
lubricious means coated on or impregnated in at least a second portion of the means for at least partially encapsulating the module, wherein the first and second portions of the means for at least partially encapsulating the module are different sides, and wherein at least one of the anti-infection means or the lubricious means is only coated on or impregnated in one side of the means for at least partially encapsulating the module.

22. The implantable medical device of claim 21, wherein the means for at least partially encapsulating the module includes a substantially concave side comprising the first portion and a substantially convex side comprising the second portion.

23. The implantable medical device of claim 22, wherein the anti-infection agent is only coated on or impregnated in the substantially concave side of the means for at least partially encapsulating the module.

24. The implantable medical device of claim 22, wherein the lubricious material is only on the substantially convex side of the means for at least partially encapsulating the module.

25. The implantable medical device of claim 21, wherein the module comprises a first module comprising a first housing, the implantable medical device further comprising a second module comprising a second housing, wherein the means for at least partially encapsulating the first module integrates the first and second module into a single structure and provides a smooth interface between the first and second housings and tissue of the patient.

26. A method comprising:
fabricating a module comprising a housing containing at least a portion of the electronics for providing monitoring of or therapy to a patient;
applying an anti-infection agent to at least a first portion of the housing; and
applying a lubricious material to at least a second portion of the housing, wherein the first and second portions of the housing are different sides, and wherein at least one of the anti-infection agent or the lubricious material is only applied to one side of the housing.

27. The method of claim 26, wherein applying an anti-infection agent to the at least the first portion of the housing comprises spraying an anti-infection agent onto the at least the first portion of the housing.

28. The method of claim 26, wherein applying an anti-infection agent to the at least the first portion of the housing comprises placing the at least the first portion of the housing into the anti-infection agent.

29. The method of claim 26, wherein applying an anti-infection agent to the at least the first portion of the housing comprises incorporating the anti-infection agent into a polymer layer and attaching the polymer layer to the at least the first portion of the housing.

30. The method of claim 26, wherein applying an anti-infection agent to the at least the first portion of the housing comprises applying the anti-infection agent to only one side of the housing.

31. A method comprising:
fabricating a member configured to provide a smooth interface between an implantable medical device and tissue of a patient;
fabricating a module containing at least a portion of the electronics for providing monitoring of or therapy to the patient;
at least partially encapsulating the module with the member;
applying a lubricious coating to at least a first portion of the member; and
applying an anti-infection agent to at least a second portion of the member, wherein the first and second portions of the member are different sides, and wherein at least one of the anti-infection agent or the lubricious material is only applied to one side of the member.

32. The method of claim 31, wherein applying an anti-infection agent to the at least the first portion of the member comprises spraying an anti-infection agent onto the at least the first portion of the member.

33. The method of claim 31, wherein applying an anti-infection agent to the at least the first portion of the member comprises placing the at least the first portion of the member into the anti-infection agent.

34. The method of claim 31, wherein applying an anti-infection agent to the at least the first portion of the member comprises incorporating the anti-infection agent into a polymer layer and attaching the polymer layer to the at least the first portion of the member.

35. The method of claim 34, wherein the polymer layer comprises the lubricious material.

36. The method of claim 31, wherein applying an anti-infection agent to the at least the first portion of the member comprises compounding the anti-infection agent with the at least the first portion of the member.

37. The method of claim 31, wherein applying an anti-infection agent to the at least the first portion of the housing comprises applying the anti-infection agent to only one side of the member.

38. The method of claim 31, wherein applying a lubricious material to the at least the second portion of the housing comprises applying the lubricious material to only one side of the member.

* * * * *